(12) United States Patent
Prossnitz et al.

(10) Patent No.: US 8,487,100 B2
(45) Date of Patent: Jul. 16, 2013

(54) COMPOUNDS FOR BINDING TO ER ALPHA/BETA AND GPR30, METHODS OF TREATING DISEASE STATES AND CONDITIONS MEDIATED THROUGH THESE RECEPTORS AND IDENTIFICATION THEREOF

(75) Inventors: Eric R Prossnitz, Albuquerque, NM (US); Sergey E Tkatchenko, San Diego, CA (US); Chetana M Revankar, Arlington, VA (US); Larry A Sklar, Albuquerque, NM (US); Jeffrey B Arterburn, Las Cruces, NM (US); Daniel F Cimino, Tijeras, NM (US); Tudor I Oprea, Albuquerque, NM (US); Cristian-George Bologa, Albuquerque, NM (US); Bruce S Edwards, Albuquerque, NM (US); Alexander Kiselyov, San Diego, CA (US); Susan M Young, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 197 days.

(21) Appl. No.: 12/967,871

(22) Filed: Dec. 14, 2010

(65) Prior Publication Data
US 2011/0092533 A1    Apr. 21, 2011

Related U.S. Application Data

(62) Division of application No. 11/497,751, filed on Aug. 2, 2006, now Pat. No. 7,875,721.

(60) Provisional application No. 60/705,516, filed on Aug. 4, 2005.

(51) Int. Cl.
    *A61K 31/4375*   (2006.01)
    *C07D 221/06*    (2006.01)

(52) U.S. Cl.
    USPC .......................................... 546/79; 514/290

(58) Field of Classification Search
    USPC .......................................... 546/79; 514/290
    See application file for complete search history.

(56) References Cited

FOREIGN PATENT DOCUMENTS

| GB | 610415 | 10/1948 |
|---|---|---|
| WO | 9834111 A1 | 8/1998 |
| WO | 0116357 A2 | 3/2001 |
| WO | 03015715 A2 | 2/2003 |
| WO | 2005063735 A1 | 2/2008 |

OTHER PUBLICATIONS

Nayak TK, et al., Influence of Charge on Cell Permeability and Tumor Imaging of GPR30-Targeted In-111-Labeled Nonsteroidal Imaging Agents. ACS Chemical Biology 2010, 5:681-690.
Ramesh C, et al., Synthesis and Characterization of Iodinated Tetrahydroquinolines Targeting the G Protein-Coupled Estrogen Receptor GPR30. J. Med. Chem. 2010, 53:1004-1014.
Schenter RE, Medical Isotopes in the 21st Century. EIR Science & Technology 2008, (Jan. 4, 2008) pp. 66-69.
Mamalis. Some Heterocyclic N-Oxides. J.Chem . Soc. 1950. pp. 703-711.
Burai et al., Highly efficient synthesis and characterization of the GPR30-selective agonist G-1 and related tetrahydroquinoline analogs. Organic and Biomolecular Chemistry 2010. vol. 8 pp. 2252-2259.
Dorwald FA, Side Reactions in Organic Synthesis. 2005. Wiley:VCH, Weinheim p. IX of Preface.
Bradsher CK. Aromatic cyclodehydration. LI. Phenanthridizinium derivatives beariing a carboxyethyl group. Journal of Organic Chemistry 1963. vol. 28. pp. 81-82.
Jaber N. Tandem Michael imino-aldol reactions catalysed by samarium diiodide. Tetrahedron Letters 2001. vol. 42. pp. 9157-9159.
Ravindranath N et al. A facile and convenient three-component coupling protocol for the synthesis of pyrano- and furoquinololines. Chemistry Letters 2003. vol. 32. pp. 222-223.
Srinivas Kvns et al. An efficient one-pot synthesis of pyrano-furoquinolines employing two reusable solid acids as heterogeneous catalysts. Synett 2004, pp. 1715-1718.

*Primary Examiner* — Rita Desai
(74) *Attorney, Agent, or Firm* — Henry D. Coleman; R. Neil Sudol

(57) ABSTRACT

The current invention is in the field of molecular biology/pharmacology and provides compounds which modulate the effects of GPR30 as well as the classical estrogen receptors alpha and beta (ERα and ERβ). These compounds may function as agonists and/or antagonists of one or more of the disclosed estrogen receptors. Diseases which are mediated through one or more of these receptors include cancer (particularly breast, reproductive and other hormone-dependent cancers, leukemia, colon cancer, prostate cancer), reproductive (genito-urological) including endometritis, prostatitis, polycystic ovarian syndrome, bladder control, hormone-related disorders, hearing disorders, cardiovascular conditions including hot flashes and profuse sweating, hypertension, stroke, obesity, osteoporosis, hematologic diseases, vascular diseases or conditions such as venous thrombosis, atherosclerosis, among numerous others and disorders of the central and peripheral nervous system, including depression, insomnia, anxiety, multiple sclerosis, neuropathy, neurodegenerative disoders such as Parkinson's disease and Alzheimer's disease, as well as inflammatory bowel disease, Crohn's disease, coeliac (celiac) disease and related disorders of the intestine. A contraceptive indication to prevent or reduce the likelihood of pregnancy after intercourse is a further aspect of the present invention.

2 Claims, 8 Drawing Sheets

Exemplary Compounds According to the Present Invention

Further Exemplary Compounds

Further Exemplary Compounds

Further Exemplary Compounds

Scheme I

Structure of oxidized versions of the G-1 compound

Ring A Modified Series of the G-Scaffold

RING B-D Modifications to the G-Scaffold

COMPOUNDS FOR BINDING TO ER ALPHA/BETA AND GPR30, METHODS OF TREATING DISEASE STATES AND CONDITIONS MEDIATED THROUGH THESE RECEPTORS AND IDENTIFICATION THEREOF

RELATED APPLICATIONS

This application claims priority from U.S. patent application Ser. No. 11/497,751, filed Aug. 2, 2006, of which the present application is a divisional, and of U.S. Provisional Application No. 60/705,516, filed Aug. 4, 2005, the entire contents of these two applications being incorporated by reference herein.

GOVERNMENT INTEREST STATEMENT

This invention was made with government support under grant numbers AI036357 and GM060799 (EB000264) awarded by the National Institutes of Health. The U.S. government has certain rights in the invention.

FIELD OF THE INVENTION

The present invention relates to compounds which modulate one or more of ERalpha/beta and GPR30 receptors, to pharmaceutical compositions based upon those compounds and to methods of treating disease states and conditions mediated through these receptors and related methods thereof.

BACKGROUND OF THE INVENTION

Estrogens mediate multiple complex physiological responses throughout the body. The responses are in turn mediated through the binding of estrogen to receptors. The classical receptors for steroids such as estrogen are soluble cytoplasmic/nuclear proteins that function as transcription factors. These receptors are known as estrogen receptor alpha and beta (two closely related proteins) that mediate transcriptional activity as well as rapid cellular signaling. GPR30 is a 7-transmembrane G protein-coupled receptor that has previously been suggested by Filardo et al., to mediate estrogen-dependent signal transduction. We have recently demonstrated that GPR30 is an intracellular protein, found in the endoplasmic reticulum, which binds estrogen with high affinity ($K_d$ ~6 nM) and mediates rapid cellular responses including calcium mobilization and phosphatidylinositol 3,4,5 trisphosphate production in the nucleus.

The current invention is in the field of molecular biology/pharmacology and provides compounds which modulate the effects of GPR30 as well as the classical estrogen receptors alpha and beta (ERα and ERβ). These compounds may function as agonists and/or antagonists of one or more of the disclosed estrogen receptors. Diseases which are mediated through one or more of these receptors include cancer (particularly breast, reproductive and other hormone-dependent cancers, leukemia, colon cancer, prostate cancer), reproductive (genito-urological) including endometreitis, prostatitis, polycystic ovarian syndrome, bladder control, hormone-related disorders, hearing disorders, cardiovascular conditions including hot flashes and profuse sweating, hypertension, stroke, obesity, osteoporosis, hematologic diseases, vascular diseases or conditions such as venous thrombosis, atherosclerosis, among numerous others and disorders of the central and peripheral nervous system, including depression, insomnia, anxiety, neuropathy, multiple sclerosis, neurodegenerative disoders such as Parkinson's disease and Alzheimer's disease, as well as inflammatory bowel disease, Crohn's disease, coeliac (celiac) disease and related disorders of the intestine. Compounds according to the present invention may also be used as contraceptive agents to prevent or decrease the likelihood that a woman will become pregnant as a consequence of intercourse.

The invention relates to compounds which have been identified as being agonists or antagonists to one or more of these receptors and represent compounds which may be used to treat any one or more diseases or conditions which are mediated through these receptors. These compounds, due to their ability to bind to GPR30 and/or one or both of estrogen receptors (alpha and beta) are useful for the treatment or prevention of the diseases which are mediated through GPR30 and/or one or both of the alpha and beta estrogen receptors.

BRIEF DESCRIPTION OF THE INVENTION

Figure 1A:
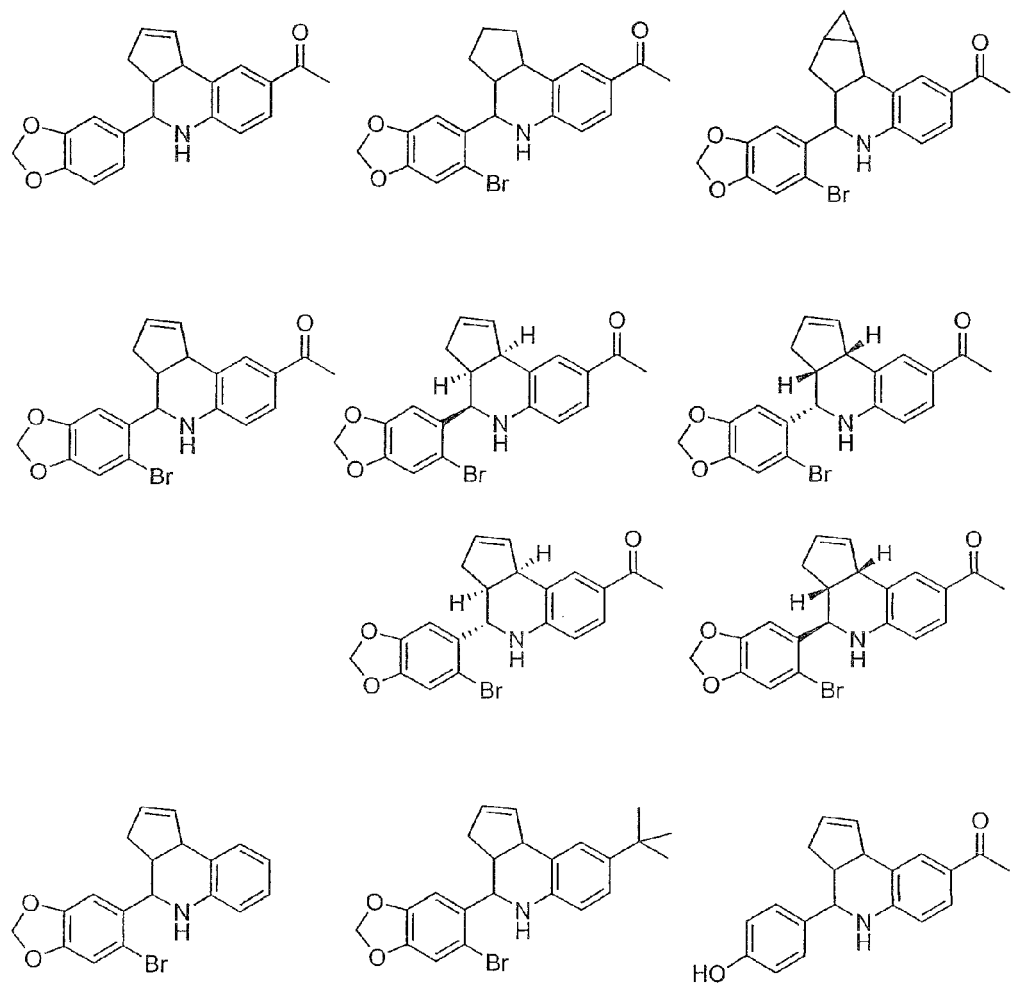
FIG. 1A-D shows numerous exemplary compounds according to the present invention.
Figure 1B:
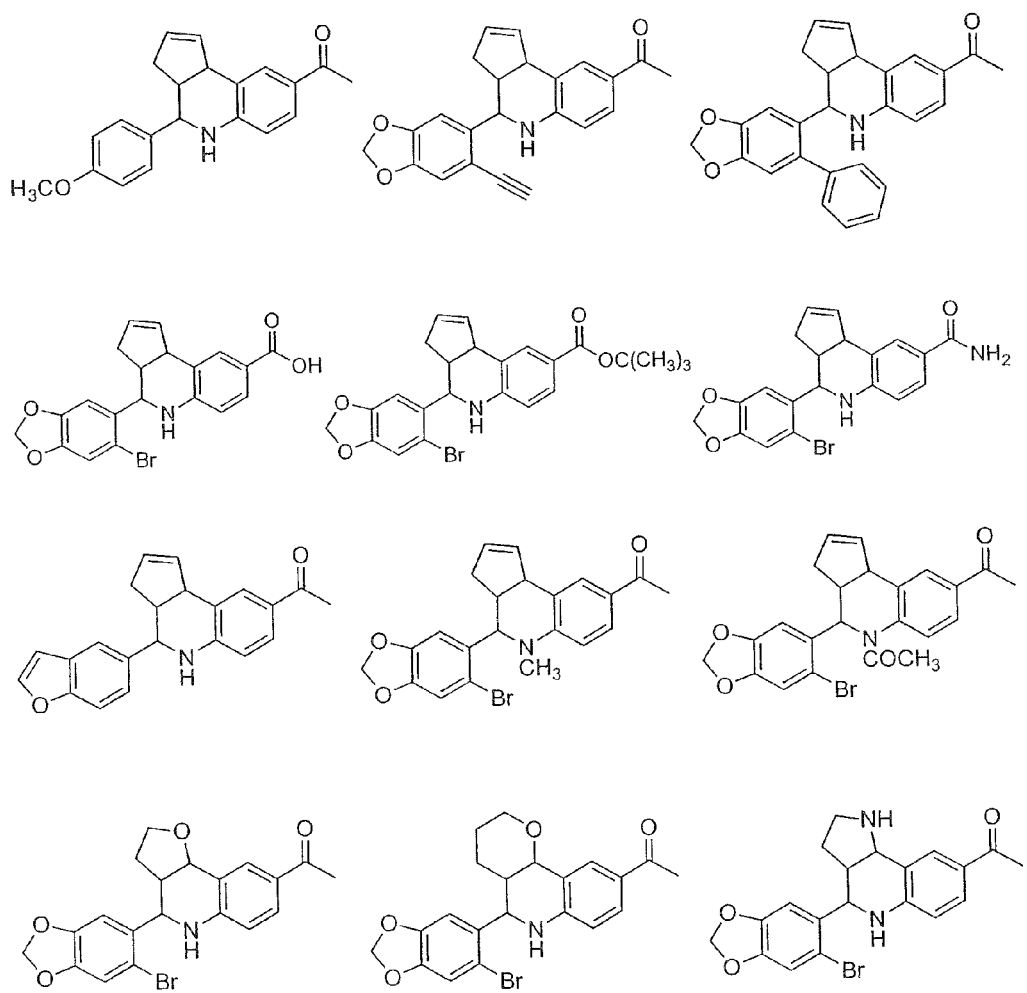
Figure 1C:
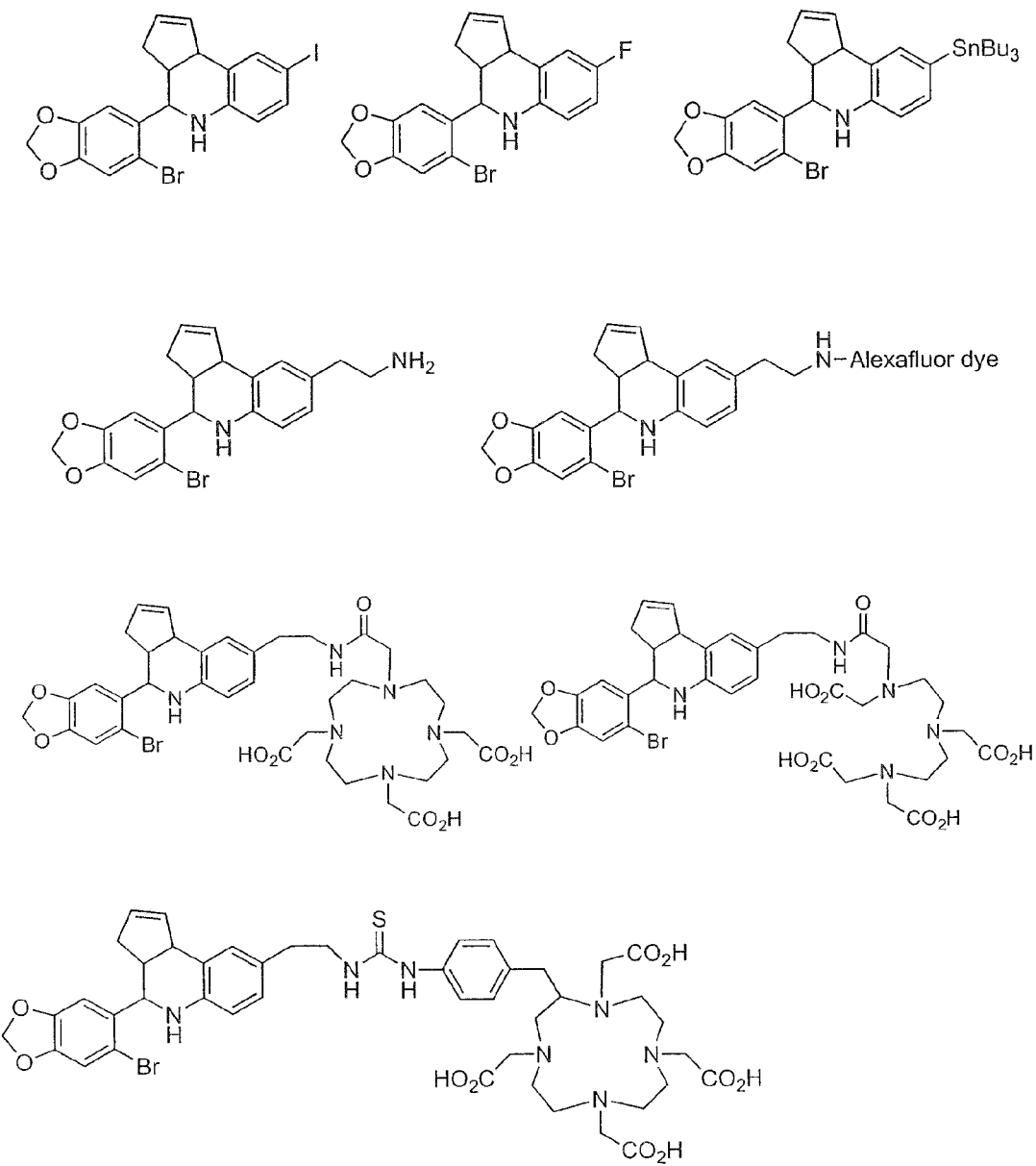
Figure 1D:
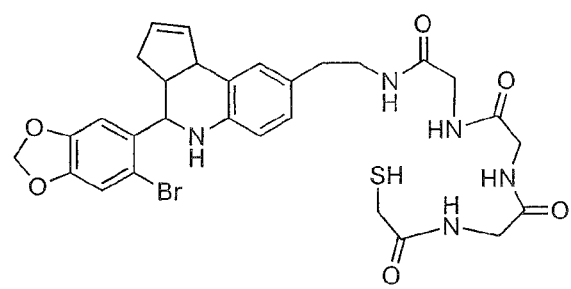
Figure 1D:
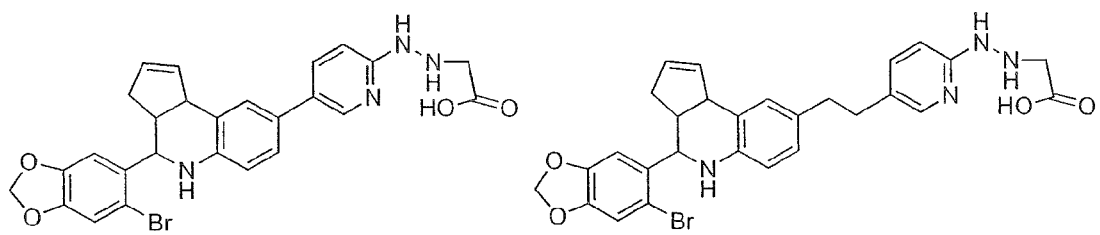
Figure 1D:
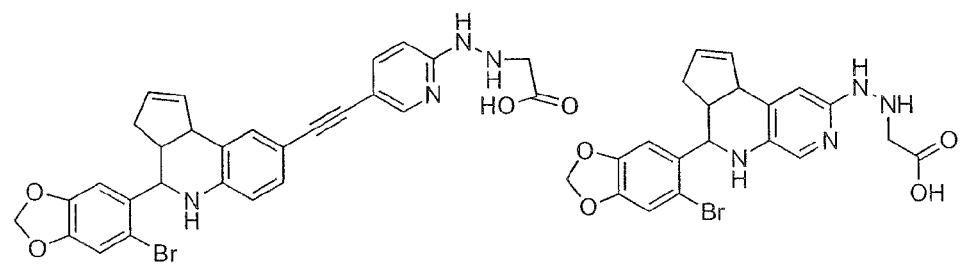
Figure 2:
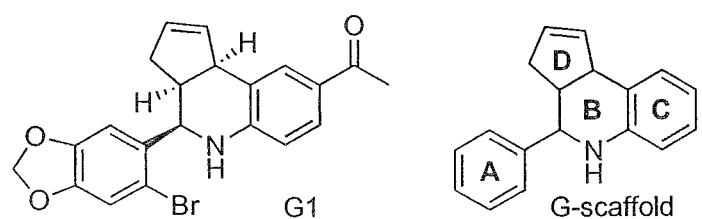
FIG. 2 shows the compound G1 and the G-scaffold according to the present invention.

The present invention relates to compounds according to the chemical structure I:

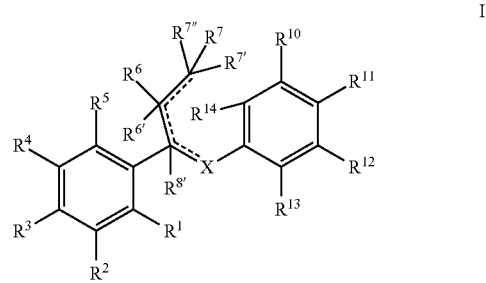

Where X is =N—, O, S, or N—R, with the proviso that when X is N—R and R is a bond, N together with $R^1$ forms a 5- to 7-membered optionally substituted heterocyclic group;

R is a bond, H, OH, $NO_2$, an optionally substituted $C_1$-$C_6$ hydrocarbyl, preferably an optionally substituted alkyl, an optionally substituted aryl, an optionally substituted heteroaryl, an optionally substituted heterocycle, an optionally substituted —C(O)—($C_1$-$C_6$) alkyl (amide), an optionally substituted —C(O)—O—($C_1$-$C_6$) alkyl (urethane), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH (heteroaryl), an optionally substituted —C(O)—N(diheteroaryl), an optionally substituted —C(O)—NH(heterocycle) or an optionally substituted —C(O)—N (diheterocycle);

$R^1$, $R^2$ and $R^5$ are each independently selected from H, OH, $NO_2$, halogen (F, Br, Cl or I), a $C_1$-$C_6$ optionally substituted carboxylic acid group, an optionally substituted O—($C_1$-$C_6$) alkyl, optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N (diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocycle);

$R^3$ and $R^4$ are each independently selected from H, OH, $NO_2$, halogen (F, Br, Cl or I), a $C_1$-$C_6$ optionally substituted carboxylic acid group, an optionally substituted O—($C_1$-$C_6$) alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N (diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl) or $R^3$ and $R^4$ together form a 5- or 6-membered optionally substituted carbocyclic (which may be saturated or unsaturated), optionally substituted aryl, optionally substituted heteroaryl or optionally substituted heterocyclic group;

$R^6$ and $R^7$ are each independently absent or are selected from H, OH, $NO_2$, halogen (F, Br, Cl or I), a $C_1$-$C_6$ optionally substituted carboxylic acid group, an optionally substituted O—($C_1$-$C_6$)alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH (heteroaryl), an optionally substituted —C(O)—N(diheteroaryl), an optionally substituted —C(O)—NH(heterocycle) or an optionally substituted —C(O)—N(diheteroaryl), or together $R^6$ and $R^7$ form a 4-, 5-, 6- or 7-membered optionally substituted carbocyclic (which may be saturated or unsaturated), an optionally substituted aryl, optionally substituted heteroaryl or optionally substituted heterocyclic group, or a 5- to 9-membered optionally substituted carbocyclic or heterocyclic bicyclic group, with the proviso that $R^7$ is not absent when both $R^{7'}$ and $R^{7''}$ are also absent;

$R^{6'}$ is absent, H, a $C_1$-$C_6$ optionally substituted hydrocarbyl group (preferably H, $CH_3$ or $CH_2CH_3$) or together with $R^6$ forms a =O group;

$R^{7'}$ is absent, H, optionally substituted hydrocarbyl group (preferably H, $CH_3$ or $CH_2CH_3$), or together with $R^7$ forms a =O group;

$R^{7''}$ is absent, H, OH, halogen (F, Br, Cl or I), an optionally substituted O—($C_1$-$C_6$)alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH (heteroaryl), an optionally substituted —C(O)—N(diheteroaryl), an optionally substituted —C(O)—NH(heterocycle) or an optionally substituted —C(O)—N(diheteroaryl);

$R^{8'}$ is absent (when the carbon to which $R^{8'}$ is attached and the carbon to which $R^6$ is attached form an optional double bond), H, $CH_3$ or $CH_2CH_3$;

$R^{10}$, $R^{11}$, $R^{12}$ and $R^{13}$ are each independently H, OH, $NO_2$, halogen (F, Br, Cl or I), a $C_1$-$C_6$ optionally substituted carboxylic acid group, an optionally substituted O—($C_1$-$C_6$) alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N (diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl);

$R^{14}$ is H, OH, $NO_2$, halogen (F, Br, Cl or I), a $C_1$-$C_6$ optionally substituted carboxylic acid group, an optionally substituted O—($C_1$-$C_6$)alkyl, optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), a optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH (heteroaryl), an optionally substituted —C(O)—N(diheteroaryl), an optionally substituted —C(O)—NH(heterocycle) or an optionally substituted —C(O)—N (diheterocycle) or together with the carbon to which $R^7$ is attached forms a 5-, 6- or 7-membered optionally substituted carbocyclic (which may be saturated or unsaturated), optionally substituted aryl, optionally substituted heteroaryl or optionally substituted heterocyclic ring; or a stereoisomer, pharmaceutically acceptable salt, solvate, or polymorph thereof.

Preferred compounds according to the present invention relate to compounds according to the chemical structure II:

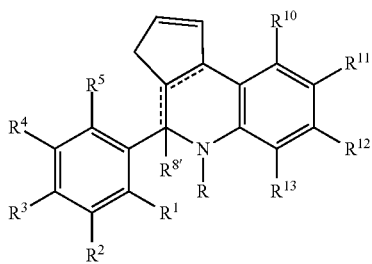

II

Where R, $R^1$, $R^2$, $R^3$, $R^4$, $R^5$, $R^{8'}$, $R^{10}$, $R^{11}$, $R^{12}$ and $R^{13}$ are as previously described above, or a stereoisomer, pharmaceutically acceptable salt, solvate, or polymorph thereof.

Preferred compounds according to the present invention also relate to compounds according to the chemical structure III:

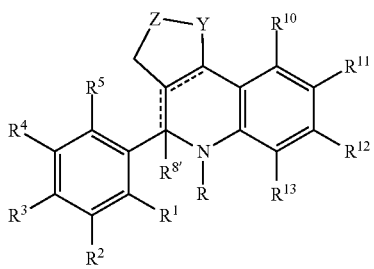

III

Where R, $R^1$, $R^2$, $R^3$, $R^4$, $R^5$, $R^{8'}$, $R^{10}$, $R^{11}$, $R^{12}$ and $R^{13}$ are as previously described above;

Y is an optionally substituted $(CH_2)_n$ group where n is 0, 1 or 2, an optionally substituted =CH— group, a C=O group, O, S, optionally substituted N—$(C_1-C_6)$alkyl, optionally substituted N-aryl, optionally substituted N-heteroaryl, optionally substituted N-heterocycle, optionally substituted N—C(O)—$(C_1-C_6)$alkyl, optionally substituted N—C(O)-aryl, optionally substituted N—C(O)-heteroaryl, optionally substituted N—C(O)-heterocycle; or a stereoisomer, pharmaceutically acceptable salt, solvate, or polymorph thereof;

Z is an optionally substituted $(CH_2)_n$ group where n is 1 or 2, an optionally substituted =CH— group, a C=O group, O, S, optionally substituted N—$(C_1-C_6)$alkyl, optionally substituted N-aryl, optionally substituted N-heteroaryl, optionally substituted N-heterocycle, optionally substituted N—C(O)—$(C_1-C_6)$alkyl, optionally substituted N—C(O)-aryl, optionally substituted N—C(O)-heteroaryl, optionally substituted N—C(O)-heterocycle; or a stereoisomer, pharmaceutically acceptable salt, solvate or polymorph thereof.

In preferred aspects of the invention, $R^3$ and $R^4$ form a five membered heterocyclic ring, preferably having two heteroatoms. Preferably, $R^3$ and $R^4$ form a furan ring. In preferred aspects of the invention, R is H or a $C_1-C_3$ alkyl group. In preferred embodiments according to the present invention, at least one of $R^1$, $R^2$, $R^5$, $R^{10}$, $R^{11}$, $R^{12}$ and $R^{13}$ and as many as three of these substituents is a halogen group. In certain preferred embodiments one of these $R^1$, $R^2$, $R^5$, $R^{10}$, $R^{11}$, $R^{12}$ and $R^{13}$ groups is a $(CH_2)_n$—$NH_2$ group, where n is 1-6, preferably 1, 2 or 3, preferably 2, where the amino group can be further reacted to provide a fluorescent label. In certain preferred embodiments, $R^1$, $R^2$ or $R^5$ is a halogen (preferably F or Br) or an optionally substituted $C_1-C_6$ hydrocarbyl group (alkyl or a $C_2-C_6$ alkenyl or alkynyl) or a —O—$(C_1-C_6$ alkyl) group and $R^{11}$ or $R^{12}$ is a halogen, a $C_2-C_6$ acyl group (preferably, acetyl), a carboxyl acid group, an optionally substituted (with at least one $C_1-C_3$ alkyl group) carboxamido group, a —O—$(C_1-C_6$ alkyl) group or an optionally substituted ester group (—C(O)O—$(C_1-C_6$ alkyl) or —O—C(O)—$(C_1-C_6$ alkyl)).

The present invention also relates to pharmaceutical compositions comprising an effective amount of one or more of the above-referenced compounds, optionally in combination with a pharmaceutically acceptable additive, carrier or excipient.

In an alternative embodiment according to the present invention, one or more positions or substituents on compounds according to the present invention are derivatized or labeled to link a fluorescent moiety. In this aspect of the invention, at a position or substituent of a compound according to the present invention, and preferably at R, $R^1$, $R^2$, $R^3$, $R^4$, $R^5$, $R^{10}$, $R^{11}$, $R^{12}$ and $R^{13}$ a fluorescent dye may be attached to the compound through a chemical linker from through carbon (carbon-carbon), amide, ester, ether, or $S(O)_n$ (where n=0, 1 or 2) bonds, among others. Representative fluorescent dyes include fluorescein, Alexa, Bodipy, Cyanin, coumarin, Dansyl, rhodamine and pyrene, among others. Specific flurescent dyes to be used in the present invention include Alex® (350, 405, 430, 488, 500, 514, 532, 546, 555, 568, 594, 610, 633, 647, 660, 680, 700 and 750), AMCA-X, Bodipy® (630/650, 650/665, FL, TMR, TR), Cascade Blue®, Dinitrophenyl, fluorescein (FAM), HEX, JOE®, cyan, Marina Blue®, Oregon Green® (488 and 514), Pacific Blue®, Pacific Orange®, Rhodamine Green®, QSY® (7, 9, 21 and 35), ROX, Rhodamine Red®, TET, Tetramethylrhodamine (TAMRA) and Texas Red®, among others, available from suppliers such as Invitrogen, Ltd (UK) and Molecular Probes, Inc. (Eugene, Oreg.), among others. One of ordinary skill will readily be able to derivatize compounds according to the present invention and link them through the above-referenced groups to fluorescent moieties provide fluorescent versions of compounds according to the present invention.

In this aspect of the invention, the present compounds are conjugated or linked to one or more of the above-described fluorescent dyes. In one aspect of the invention, compounds according to the present invention may by synthesized which contain or are modified to contain nucleophilic functional groups such as OH, SH, $NH_2$, which are coupled with reactive dyes containing electrophilic functional groups. The result is a conjugated fluorescently labeled compound according to the present invention. In another aspect of the invention, compounds according to the present invention which contain or are modified to contain electrophilic functional groups including aldehydes, ketones, inaleimide, epoxide, carboxylic acid or esters, may be coupled with nucleophilic reactive dyes to produce fluorescently labeled compounds according to the present invention. Alternatively, compounds according to the present invention which contain or are modified with or to contain bifunctional linkages such as aminohexanoic acid, succinic acid, etc. are coupled with a reactive dye accordingly to produce fluorescently labeled compounds according to the present invention. This chemistry is well developed in the art. Examples of Reactive Fluorescent Dyes:

Amine Reactive:
Fluorescein isothiocyanate
[Tetramethylrhodamine-5-(and-6)-isothiocyanate]
[6-(Fluorescein-5-carboxamido)hexanoic acid, succinimidyl ester]
[5-(and-6)-Carboxyrhodamine 6G, succinimidyl ester]
[5-(and-6)-Carboxytetramethylrhodamine, succinimidyl ester]

[6-(Tetramethylrhodamine-5-(and-6)-carboxamido) hexanoic acid, succinimidyl ester]
[5-(and-6)-Carboxyfluorescein, succinimidyl ester]
1-pyrenebutanoic acid succinimidyl ester
7-Hydroxy-4-methylcoumarin-3-acetic acid, succinimidyl ester
7-Methoxycoumarin-3-carboxylic acid, succinimidyl ester
[6-((7-Amino-4-methylcoumarin-3-acetyl)amino)hexanoic acid, succinimidyl ester]
[5-Dimethylaminonaphthalene-1-sulfonyl chloride]
[Tetramethylrhodamine-5-iodoacetamide]
[5-(((2-Iodoacetypamino)ethyl)amino)naphthalene-1-sulfonic acid]
[6-Bromoacetyl-2-dimethylaminonaphthalene]
Thiol Reactive
[N-(7-Dimethylamino-4-methylcoumarin-3-yl)maleimide]
Aldehyde, Ketone (Electrophilic) Reactive
Sulforhodamine 101 Hydrazide The present invention also relates to compounds according to the present invention wherein one or more substituents in compounds according to the present invention are isotopically labeled, including stable and radioactive isotopes. The substituents located at any substitutable position on compounds according to the present invention may possess isotopes of hydrogen (H-2, H-3), carbon (C-11, C-13, C-14), fluorine (F-18), iodine (I-123, I-125, I-131), bromine (Br-77), nitrogen (N-13, N-15), oxygen (O-15, O-18), phosphorous (P-32), sulfur (S-35), boron (B-10) as well as other stable or radioactive isotopes which do not require a chelate to attach to compounds according to the present invention. These isotopes assist in providing relevant information in bioassays, mechanistic studies and receptor ligand interactions, among others and may be used on compounds according to the present invention with well-known analytical techniques. Synthesis of these compounds may be readily performed using standard chemical synthetic techniques well-known in the art for isotopically labeling compounds.

The present invention also relates to derivatives of compounds (I, II or III) wherein one or more substituents in compounds according to the present invention provide chelating ligands or other functionality for labeling with radionuclide complexes. The substituents located at any substitutable position on compounds according to the present invention, preferably at or on R, $R^1$, $R^2$, $R^3$, $R^4$, $R^5$, $R^{10}$, $R^{11}$, $R^{12}$ and $R^{13}$ of any of the compounds of the present invention may provide chelating ligands including aminocarboxylates such as diethylenetriaminepentaacetic acid (DTPA), 1,4,7,10-tetraazacyclododecane-1,4,7,10-tetraacetic acid (DOTA), mercaptoacetyltriglycine ($MAG_3$), picolinamine-N-acetic acid, pyridin-2-ylhydrazine-N-acetic acid. Radionuclide complexes include isotopes of bismuth (Bi-213), copper (Cu-64, Cu-67), gallium (Ga-67, Ga-68), indium (In-111), lutetium (Lu-177), palladium (Pd-103), rhenium (Re-186, Re-188), technetium (Tc-99m, Tc-94), and yttrium (Y-90).

In a further embodiment, the present invention also relates to a method of detecting GPR30 receptors in a tissue sample suspected of containing GPR receptors comprising exposing said tissue sample to a compound as described above, measuring the binding of said compound to said tissue sample and comparing the results of said measuring step to at least one standard obtained by measuring the binding of said compound to at least one tissue sample known to contain GPR receptors. In another aspect of the invention, a separate or an additional tissue sample from which a standard is determined may be devoid of GPR receptors (in order to test for GPR receptors or for non-specific binding).

In yet a further embodiment of the present invention, a method of diagnosing cancer in a tissue sample suspected of being cancerous comprises exposing said tissue to a compound as described above, measuring the binding of said compound to said tissue to produce a first measurement and comparing the first measurement obtained with a standard obtained by measuring the binding of said compound with a tissue sample known to be free of cancer; wherein a first measurement which is substantially greater than said standard is indicative of cancer and a first measurement which is the same or lower than said standard is indicative of the absence of cancer in said tissue sample. In a related method, the first measurement may be compared to the binding of the compound with a similar type of tissue which is known to be cancerous wherein a measurement which is the same or higher than the standard is indicative of cancer in the tested tissue. Alternative embodiments may comprise comparing the first measurement with a standard obtained from both cancerous and non-cancerous tissue of the same type to gauge the presence of cancer in the tissue.

Exemplary Compounds of the Present Invention are set forth in FIGS. 1A-D.

Alternative specific compounds for use in the present invention include the following compounds:

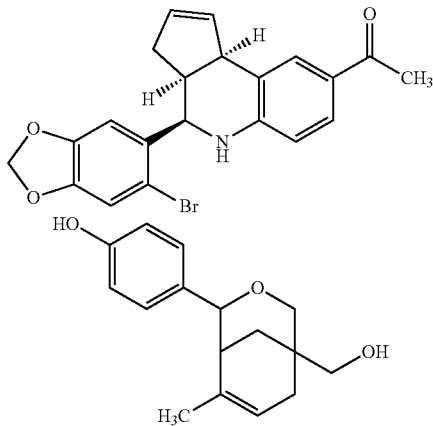

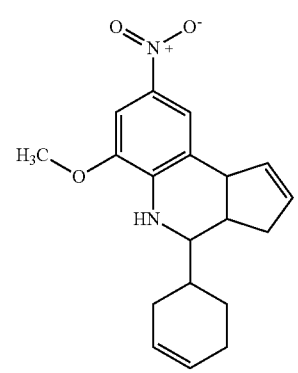

and pharmaceutically acceptable salts and derivatives thereof.

A preferred embodiment according to the present invention also relates to the following fluorescently labeled compound:

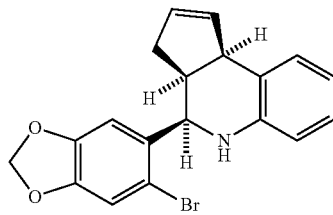
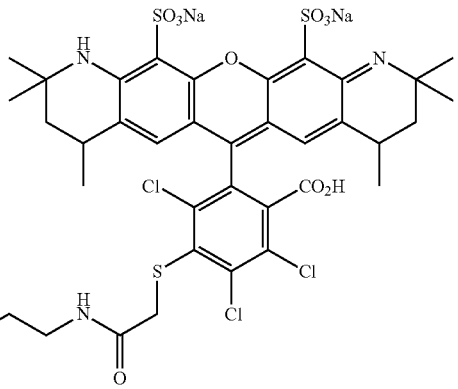

The present invention relates to compounds which preferably are agonists or antagonists of GPR30 and/or alpha and/or beta estrogen receptor and act through their action at one or more of these receptors, can be used to treat or prevent diseases or conditions which are modulated through those receptors.

The compounds according to the present invention can be used to inhibit or modulate GPR30 and/or alpha and/or beta estrogen receptors. Compounds according to the present invention have antagonist and/or agonist activity against these receptors. Compounds according to the present invention can be used to treat a number of disease states which are mediated through these receptors. These disease states or conditions include, for example, cancer (particularly breast, reproductive and other hormone-dependent cancers, leukemia, colon cancer, prostate cancer), reproductive and genitourological diseases or conditions including endometreitis, prostatitis, polycystic ovarian syndrome, bladder control, hormone-related disorders, hearing disorders, cardiovascular disease and conditions including hot flashes and profuse sweating, hypertension, stroke, ischemia, myocardial infarction, obesity, osteoporosis, restoration of lipid profile, atherosclerosis, symptoms of menopause, inflammation, rheumatoid arthritis and osteoarthritis, hematologic diseases and conditions, including lymphoproliferative disorders, myeloproliferative disorders, eosinophilia, histiocytosis, paroxysmal nocturnal hemoglobinuria, and systemic mastocytosis, vascular diseases or conditions such as venous thrombosis, embolisms, among numerous others, disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine. Compounds according to the present invention may also be used to provide contraceptive compositions to prevent or reduce the likelihood of pregnancy after intercourse.

A method of treating any one or more of the above-described diseases or conditions comprises administering to a patient in need thereof at least one compound as otherwise described herein or a pharmaceutically acceptable salt thereof, optionally in combination with a pharmaceutically acceptable carrier, additive or excipient.

DETAILED DESCRIPTION OF THE INVENTION

The following terms shall be used throughout the specification to describe the present invention. A term in which is otherwise not defined has the same meaning as one of ordinary skill within the context of the use of that term would assign to the term. Note that all terms are used in context to avoid overlap and redundancy where applicable.

The term "patient" refers to a mammal, preferably a human, in need of treatment or therapy to which compounds according to the present invention are administered in order to treat a condition or disease state modulated through the binding of a compound according to the present invention with a receptor, and in particular, GPR30 and/or estrogen receptor alpha (ERα) and/or (ERβ).

The term "GPR30 receptor" refers to a 7-transmembrane G protein-coupled receptor that mediate estrogen-dependent signal transduction. GPR30 is an intracellular protein, found in the endoplasmic reticulum, which binds estrogen with high affinity ($K_d$ ~6 nM) and mediates rapid cellular responses including calcium mobilization and phosphatidylinositol 3,4,5 trisphosphate production in the nucleus. GPR30 receptor refers to all types of GPR30 receptor, regardless of the tissue in which such receptor is found and refers to any variant thereof, including receptors of mammals (preferably, humans and domesticated mammals where veterinary applications are relevant) and variants thereof. Other names which have been used for GPR30 include CMKRL2, DRY12, FEG-1, GPCR-Br, LERGU, LERGU2, LyGPR, CEPR and MGC99678, among others.

The term "modulate" means, with respect to disease states or conditions modulated through binding of a compound according to the present invention to GPR30 and/or estrogen receptor alpha (ERα) and/or estrogen receptor beta (ERβ) to produce, either directly or indirectly, an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site).

The term "compound", as used herein, unless otherwise indicated, refers to any specific chemical compound disclosed herein and includes in context, tautomers, regioisomers (especially cis/trans), geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., cis and trans isomers) and all optical isomers of the present compounds (e.g., R and S enantiomers), as well as racemic, diastereomeric and/or other mixtures of such isomers, as well as all pharmaceutically acceptable salt forms, solvates, polymorphs and prodrug forms of the present compounds, where applicable.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The term "cancer" includes any cancer of any origin and is used to describe all cancerous disease states and embraces or encompasses the pathological process associated with malignant hematogenous, ascitic, and solid tumors. The term "cancer" and the term "tumor" used in this application is interchangeable with the term "neoplasia".

Cancer which may be treated using compositions according to the present invention include, for example, cancers of the stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, melanoma, acute leukemia, including lymphocytic leukemia, hairy cell leukemia, and acute myelogenous leukemia, Ewing's sarcoma, small cell lung cancer, choriocarcinoma, rhabdomyosarcoma, Wilms' Tumor, neuroblastoma, mouth/pharynx, oesophagus, larynx, kidney, lymphoma, among others, and in particular, breast, reproductive, ovarian, cervical, uterine, endometrial and other hormone-dependent cancers. Drug-resistant cancers are also treatable using compounds according to the present invention and represent a preferred embodiment of the present invention.

The term "anti-cancer compound" or "anti-cancer agent" is used to describe any compound (including its derivatives) which may be used to treat cancer and is used in combination with one or more of the compounds according to the present invention in the treatment of cancer. The term "second anti-cancer compound" or "second anti-cancer agent" may also apply to these agents in context. Anti-cancer agents as described hereunder are a subset of cytotoxic agents which may be used in the present invention in coadministration with compounds according to the present invention. Exemplary anti-cancer compounds for use in the present invention include anti-metabolite agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anti-cancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposidephosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. Note that one of ordinary skill in the art may readily employ any one or more of these second anti-cancer agents in combination with compounds according to the present invention to treat cancer.

The term "coadministration" or "combination therapy" is used to describe a therapy in which at least two active compounds in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include those described above, and mixtures thereof, among others. Coadministration of one of the present compounds with another anticancer agent as otherwise described herein will often result in a synergistic enhancement of the anticancer activity of the other anticancer agent, an unexpected result. One or more of the present compounds may also be coadministered with another bioactive agent (e.g., antiviral agent, antihyperproliferative disease agent, agents which treat chronic inflammatory disease, among others or as otherwise described herein), depending upon the desired therapeutic outcome and the disease state or condition treated.

The term "reproductive disorder" or "genito-uriological disorder" is used to describe diseases or conditions of the genital or urinary tract and include such conditions as benign prostatic hyperplasia, prostatitis, infertility, polycystic ovarian syndrome, sexual dysfunction, endometreitis, vaginal dryness, dyspareunia, as well as kidney and urinary complications, including bladder control, among others. Note that compounds/compositions according to the present invention also may be useful as contraceptive agents, i.e., agents which prevent or reduce the likelihood that a female will become pregnant after intercourse.

The term "hematologic disorder" is used to describe a disease or condition of blood and includes such diseases or conditions as lymphoproliferative disorders (diseases of white blood cells called T cells and B cells); myeloproliferative disorders (diseases in which too many of certain types of blood cells are made in the bone marrow); and includes four other blood disorders—eosinophilia, histiocytosis, paroxysmal nocturnal hemoglobinuria, and systemic mastocytosis, among others. Hematologic disorders are distinguishable from leukemia, which is also treated using compounds according to the present invention.

The treatment of cancer, including malignant tumors comprising administering to a patient an anti-cancer effective amount of one or more these agents is a preferred embodiment of the present invention.

"Hydrocarbon" or "hydrocarbyl" refers to any radical containing carbon and hydrogen, which may be straight, branch-chained or cyclic in nature. Hydrocarbons include linear, branched and cyclic hydrocarbons, including alkyl groups, alkylene groups and unsaturated hydrocarbon groups, which may be optionally substituted. Hydrocarbyl groups may be fully saturated or unsaturated, containing one or more double ("ene") or triple ("yne") bonds.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Other terms used to indicate substituent groups in compounds according to the present invention are as conventionally used in the art. Thus, the term alkylene aryl includes alkylene phenyl such as a benzyl group or ethylene phenyl group, alkylaryl, includes alkylphenyl such a phenyl group which has alkyl groups as substituents, etc. The bond -----, when used in chemical structures of the present application refers to a single chemical bond, which may be an optional double bond, in context.

"Aryl" refers to a substituted or unsubstituted monovalent aromatic radical having a single ring (e.g., benzene) or multiple condensed rings (e.g., naphthyl, anthracenyl, phenanthryl) and can be can be bound to compound according to the present invention at any position on the ring(s). Other examples of aryl groups include heterocyclic aromatic ring systems "heteroaryl" having one or more nitrogen, oxygen, or sulfur atoms in the ring, such as imidazole, furyl, pyrrole, pyridyl, indole and fused ring systems, among others, which may be substituted or unsubstituted.

"Alkoxy" as used herein refers to an alkyl group bound through an ether linkage; that is, an "alkoxy" group may be represented as —O-alkyl where alkyl is as defined above.

The term "cyclic" shall refer to a carbocyclic or heterocyclic group, preferably a 5- or 6-membered ring, but may include 4 and 7-membered rings. "Bicyclic" or "bicyclo" refers to bicyclic The term "heterocycle" or "heterocyclic" shall mean an optionally substituted moiety which is cyclic and contains at least one atom other than a carbon atom, such as a nitrogen, sulfur, oxygen or other atom. A heterocyclic ring shall contain up to four atoms other than carbon selected from nitrogen, sulfur and oxygen. These rings may be saturated or have unsaturated bonds. Fused rings are also contemplated by the present invention. A heterocycle according to the present invention is an optionally substituted imidazole, a piperazine (including piperazinone), piperidine, furan, pyrrole, imidazole, thiazole, oxazole or isoxazole group, among numerous others. Depending upon its use in context, a heterocyclic ring may be saturated and/or unsaturated. In instances where a heterocyclic ring is fully unsaturated, there is overlap with the term "heteroaryl".

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or halogen (fluoro) group, among others), preferably an alkyl (generally, no greater than about 12 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen (especially fluoro), thiol, hydroxyl, carboxyl, oxygen (to form a keto group), $C_1$-$C_8$ alkoxy, CN, nitro, an optionally substituted amine (e.g., an alkyleneamine or a $C_1$-$C_6$ monoalkyl or dialkyl amine), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ thioether, amide (amido or carboxamido), substituted amide (especially mono- or di-alkylamide) or alkyleneamine, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various optionally substituted moieties may be substituted with 5 or more substituents, preferably no more than 3 substituents and preferably from 1 to 3 substituents.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention all geometric isomers as mixtures (impure) or pure isomers are contemplated by the present invention. In preferred aspects, the present invention is directed to pure geometric isomers.

The term "optical isomer" is used to describe either of two kinds of optically active 3-dimensional isomers (stereoisomers). One kind is represented by minor-image structures called enantiomers, which result from the presence of one or more asymmetric carbon atoms. The other kind is exemplified by diastereomers, which are not minor images and which contain at least two asymmetric carbon atoms. Thus, such compounds have $2_n$ optical isomers, where n is the number of asymmetric carbon atoms. In the present invention all optical isomers in impure (i.e., as mixtures) or pure or substantially pure form (such as enantiomerically enriched or as separated diastereomers) are contemplated by the present invention. In certain aspects, the pure enantiomer or diastereomer is the preferred compound.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

Regardless of the mechanism, the compounds of the present invention may be used to treat disease states or conditions in patients or subjects who suffer from those conditions or disease states or are at risk for those conditions. In this method a compound in an effective amount is administered to a patient in need of therapy to treat the condition(s) or disease state(s). These disease states and conditions include, for example, cancer (particularly breast, reproductive and other hormone-dependent cancers, leukemia, colon cancer, prostate cancer), reproductive and genito-urological diseases or conditions including endometreitis, prostatitis, polycystic ovarian syndrome, bladder control, hormone-related disorders, hearing disorders, cardiovascular disease and conditions including hot flashes and profuse sweating, hypertension, stroke, ischemia, myocardial infarction, obesity, osteoporosis, restoration of lipid profile, atherosclerosis, symptoms of menopause, inflammation, rheumatoid arthritis and osteoarthritis, hematologic diseases and conditions, including lymphoproliferative disorders, myeloproliferative disorders, eosinophilia, histiocytosis, paroxysmal nocturnal hemoglobinuria, and systemic mastocytosis, vascular diseases or conditions such as venous thrombosis, embolisms, among numerous others, disorders of the central and peripheral nervous system, including depression, insomnia, anxiety, neuropathy, multiple sclerosis, neurodegenerative disorders such as Parkinson's disease and Alzheimer's disease, as well as inflammatory bowel disease, Crohn's disease, coeliac (celiac) disease and related disorders of the intestine. In a contraceptive embodiment, the present compounds may also be used to prevent or reduce the likelihood that a woman will become pregnant after intercourse by administering to said women before or after intercourse an effective amount of one or more compounds according to the present invention.

Compositions according to the present invention may be administered by any conventional means known in the art. Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalatiosno intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms for topical administration include ointments, powders, sprays and inhalants. The compound(s) are admixed under sterile conditions with a physiologically acceptable carrier, and any preservatives, buffers, and/or propellants that may be required. Opthalmic formulations, eye ointments, powders, and solutions are also contemplated as being within the scope of this invention.

Chemical Synthesis
General Procedure for Preparation of Tetrahydroquinoline Derivatives (G-Scaffold)

The three component cyclization reaction of aldehyde, amine and ene components used for the synthesis of the tetrahydro-3H-cyclopenta[c]quinoline structure of G1 and derivatives may be catalyzed by a variety of protic and Lewis acids. Scandium(III) triflate (Sc(OTf)$_3$) was a particularly effective catalyst for the synthesis of the derivatives included in this invention and typically provided fast reaction times and high product yields.

In general, an aldehyde or ketone as pictured in the scheme presented below is added to a solutions containing an amine and optionally, a third compound such as a diene or other unsaturated compound, as appropriate to reflect the various substitutions on the final compound of interest. The condensation reactions proceed in the presence of catalyst in solvent at varying temperatures, depending on the reactants, their functional groups and the type of reaction employed. Note that the synthetic method relies in general on the use of a condensation reaction between an amine and an aldehyde or ketone (depending upon the final desired compound) and a subsequent/simulatenous reaction to derivatize the newly formed Schiff's base or other intermediate (as appropriate) to produce the final compound. It is noted here that various components may be added to the general reaction scheme to produce final product and chemical steps may be added as appropriate to introduce substituents and other groups to produce final product. In certain instances, blocking groups or other groups which are inactive under certain reaction conditions, but which can be removed without interfering with the basic chemistry previously introduced, may be used to produce compounds according to the present invention. Various modifications to the general synthetic scheme may be readily accomplished by those of ordinary skill using various well-known general synthetic methods.

The general synthetic approach for construction of the tetrahydro-3H-cyclopenta[c]quinoline scaffold is represented in FIG. 1, Scheme I. This three component coupling procedure combines an aniline C and aldehyde A to yield an intermediate imine, followed by cyclization with ene D. Initially described by Povarov, *Russ Chem Rev* 36, 656-70, (1967), the overall transformation can also be described formally as an aza-Diels Alder reaction and may be conducted sequentially or in one step. This reaction is a versatile synthetic method that accommodates a wide variety of substituted components and can be catalyzed by protic or Lewis acids. See, for example, Babu, and Perumal, P. T. (1998), *Tetrahedron* 54, 1627-38, (1998); Ma, et al., *Journal of Organic Chemistry* 64, 6462-7 (1999); Crousse, et al, *Journal of Organic Chemistry* 16, 5009-13, (2000); Collin, et al., *Tetrahedron Letters* 42, 7405-7, (2001); Yadav, et al., *Tetrahedron* 59, 1599-604, (2003); Powell, et al,. *Organic Letters* 4, 2913-6, (2002); Zhang and Li, *Journal of Organic Chemistry* 67, 3969-71, (2002); Chen and Li, *Green Chemistry* 5, 627-9, (2003); Li, et al., *Tetrahedron Letters* 44, 153-6, (2003); Powell and Batey, *Tetrahedron Letters* 44, 7569-73, (2003); Yadav, et al, *Synlett* 2, 240-2, (2001); Twin and Batey, *Organic Letters* 6, 4913-6, (2004); Akiyama, et al., *Chemistry Letters* 33, 922-3, (2004); Nagarajan, et al., *Synthesis* 1, 69-74 (2004); Kumar, et al., *Synthesis* 6, 949-59 2004); Hermitage, et al., *Organic & Biomolecular Chemistry* 2, 2451-60, (2004); Tolstikov, et al., *Heteroatom Chemistry* 16, 605-12 (2005); Hadden, et al., *Tetrahedron* 62, 3977-84, (2006); Ramesh, et al., *Synthetic Communications* 36, 1431-6, (2006). The resulting G-scaffold contains three stereogenic centers, however, the "syn" or "endo" diastereomers are typically fowled with high selectivity and exhibit a characteristic 1H-NMR coupling pattern of the B ring hydrogen atoms that can be easily recognized.

By way of example, a solution of the catalyst Sc(OTf)$_3$ (49.2 mg, 0.10 mmol, 10 mol %) in anhydrous acetonitrile (0.4 mL) was added to the mixture of aldehyde (A, 1 mmol), amine (C, 1 mmol) and ene (D, 5 mmol) in acetonitrile (4 mL) The reaction was stirred at ambient temperature (~23° C.) and the progress was monitored by thin layer chromatography. Reaction times typically ranged from 0.5 hr to 5 hr for completion. The reaction mixture was worked up by removal of solvent and other volatiles by evaporation under reduced pressure. The crude product was purified by preparative column chromatography using silica gel ($SiO_2$) eluted with EtOAc/hexane (polar phase composition 5-30% EtOAc depending on product Rf). The fractions containing pure product were evaporated in vacuo. The structural identity and purity were characterized by spectroscopic methods ($^1$H and $^{13}$C NMR, FT-IR) and HPLC-MS/UV. Compound G1 can be readily synthesized in this manner.

Synthesis of a G-Scaffold Library.

Figure 3:
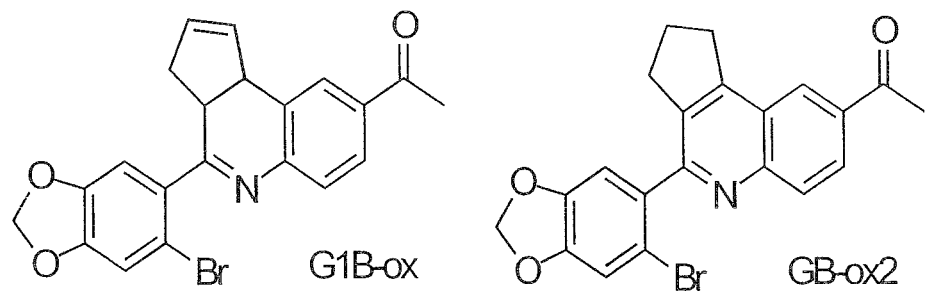
FIG. 3 shows oxidized versions of the G1 compound.

Complete characterization of the structural features responsible for G-1 binding affinity to GPR30 is achieved through the synthesis of selected cyclopenta[c]quinolines. We recently prepared G-1 on a multigram scale and resolved the two syn-enantiomers using chiral reverse phase preparative HPLC. Additional screening and activation studies enable correlation of receptor biology with the absolute enantiomeric configuration of G-1. The isolation of the minor G-1-"anti" diastereomer is accomplished using $SmI_2$ catalyst. These conditions typically yield increased relative amounts of the anti stereoisomer (Collin, et al., *Tetrahedron Letters* 42, 7405-7, (2001)) and we have found that G-1-anti is produced in 10% yield and can be isolated by preparative HPLC. Additional selected members of the G-1 series (FIG. 3) include the oxidized derivative G-1B-ox that is prepared by controlled oxidation of G-1 with $MnO_2$ [See, Lucchini, et al., *Journal of Heterocyclic Chemistry* 23, 1135-9, 1986] and the quinoline GB-ox2 that will be obtained by alkene isomerization and oxidation [Fadel, et al., *Tetrahedron Letters* 45, 5905-8 (1986)]. These compounds will help to elucidate the role of the B-ring nitrogen in potential hydrogen bonding and how altered planarity of the cyclopenta[c]quinoline affects interactions with the receptor.

A-Ring Modifications of the G-Scaffold.

Figure 4:
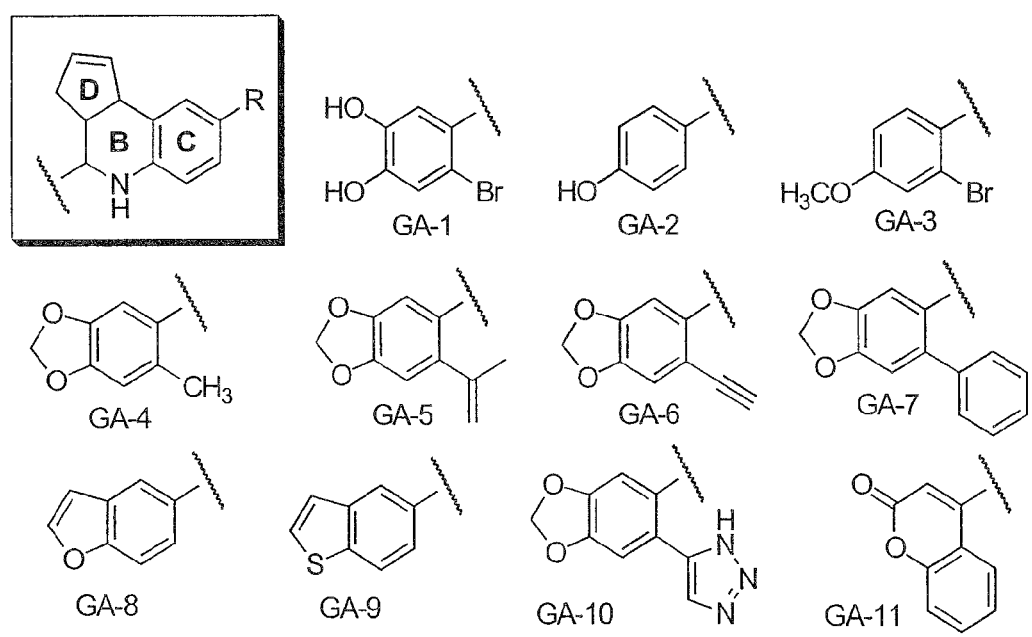
FIGS. 4 and 5 show synthetic schemes associated with derivatizing the G-scaffold of the present invention.

Variations of the identity and substitution pattern of functional groups on the A-ring are predicted to significantly affect GPR30 binding affinity and activation profiles. The library of G-derivatives will include the compounds illustrated in FIG. 4. Cleavage of the dioxolane group of G-1 with $AlCl_3$ will provide the catechol GA-1 [Reitz, et al., *Journal of Organic Chemistry* 46, 4859-63 (1981)]. The free phenol GA-2 and methoxy derivative GA-3 will be prepared by three component coupling with p-hydroxybenzaldehyde. Replacement of the bromide substituent of G-1 with lithium dimethylcuprate will provide the methyl derivative GA-4. Palladium-catalyzed Suzuki or Sonogashira coupling procedures with G-1 will provide alkene GA-5, aryl derivative GA-7, and the alkyne GA-6, respectively. Protection of the amine may be necessary to avoid cyclopalladation of the benzylic amine under these conditions, and can be accomplished by formation of the trifluoroacetamide. We have extensive experience with these types of C—C coupling reactions and heterocyclic amine substrates. Benzofuran GA-8, benzothiophene GA-9, and coumarin GA-11 derivatives will be synthesized from the corresponding aldehydes in the Povarov cyclization. Triazole GA-10 will be prepared by azide cycloaddition to alkyne GA-6. This series of A-ring substituted derivatives will probe the steric and electronic features of GPR30 binding and activation and is expected to yield valuable information for SAR/QSAR analyses that will enable the development of potent GPR30 antagonists.

B-D Ring Modifications of the G-Scaffold.

Figure 5:
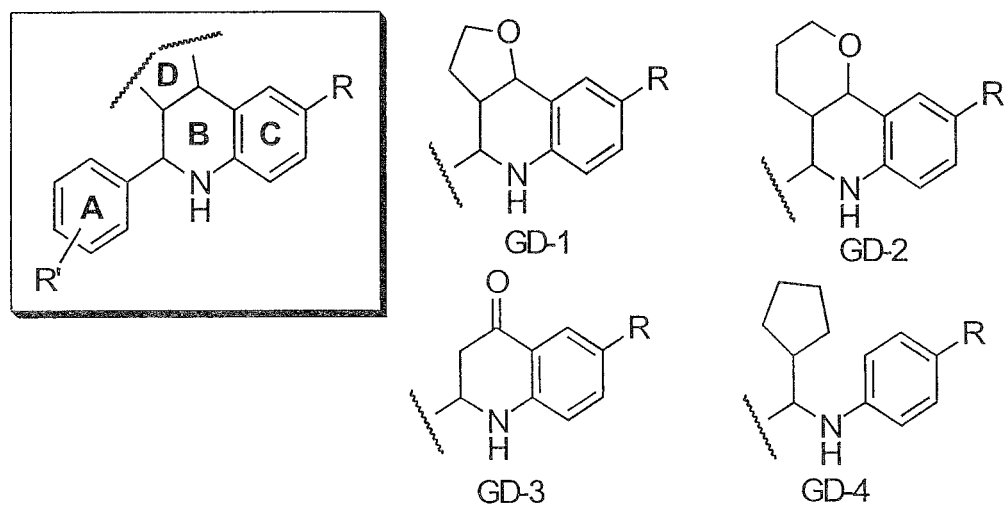

Structural modification of the cyclopenta[c]quinoline moiety of the G-scaffold is also expected to significantly affect GPR30 binding affinity. The reduced affinity was observed from increasing the steric volume of ring D as discussed above. We will investigate the effect of increasing the polarity by introducing an oxygen atom into the D-ring (FIG. 5). The tetrahydro furan derivative GD-1 will be synthesized from the three component cyclization with 2,3-dihydrofuran. The homologated sterically larger 6-membered ring tetrahydropyran GD-2 will be prepared analogously from the dihydropyran. Replacement of the D-ring with ketone in GD-3 will be accomplished by cyclization with p-methoxybenzyl vinyl ether, followed by deprotection and oxidation. This compound will also provide opportunities for diversification through nucleophilic additions, alkene formation, enolate alkylation, and reductive amination chemistry. The effect of increased flexibility will be evaluated by eliminating the B-ring in compound GD-4. This derivative will be synthesized by indium mediated addition of iodocyclopentane to the corresponding imine that we have used in the synthesis of G-1 [Miyabe, et al., *Tetrahedron* 60, 4227-35 (2004)].

The compounds identified as synthetic targets in this section represent the first iteration of structural modifications for the purpose of identifying structure-activity relationships of the G-scaffold and GPR30 binding and activation. Our initial studies have identified this tetracyclic core as a promising scaffold for optimization of GPR30 binding and activation that is distinguished from classical estrogen receptors. This investigation will use the results from the first series of synthetic G-derivatives to characterize the GPR30 binding interactions of G-1, and identify initial leads directed towards antagonism. It is important to emphasize that these synthetic objectives will be achieved through extensive interaction with the computational and screening components of this investigation. The input from the ligand-based virtual screening approach and the developing QSAR model will focus our efforts to synthesize additional series of GPR30 antagonists that maintain selectivity over ER subtypes of at least 3 orders of magnitude. These design considerations will also include input from medicinal chemistry that prioritizes structures with promising drug-like properties of adsorption, distribution, metabolism and excretion. Additional considerations beyond the well recognized "rule of 5" associate favorable characteristics of drugs with 0-2 hydrogen bond donors, 2-9 hydrogen bond acceptors, 1-4 rings, and 2-8 rotatable bonds [T. Oprea, *J Comput Aided Mol Des* 14, 251-64 (2004)]. Compound solubility is determined using a flow cytometric approach that uses light scatter to measure particulates. The progression of this investigation provides opportunities for scaffold-hopping to follow active leads with structures that deviate significantly from our initial lead G-1.

EXAMPLES

Identifying a Pharmacophore

In order to identify a pharmacophore and compounds according to the present invention, the following binding assay was performed using a library of compounds.

The binding assay is carried out as follows. COST cells transfected to express either nuclear estrogen receptor (ER)-GFP or GPR30-GFP are serum starved for 24 h before the assay. Cells are treated with 2 nM E2-Alexa 633 diluted in permeabilization buffer (0.025% saponin, 5 mM EGTA, 100 mM NaCl and 1 mM $MgCl_2$ in 80 mM piperazine-N—N'-bis (2-ethane sulfonic acid)-KOH (pH 6.8)) for 10 min at 37° C. The cells are fixed with chilled 2% PFA in PBS with 1 mM CaCl$_2$ and 1 mM MgCl$_2$ for 15 mM at 37° C. For flow cytometric analysis of E2-Alexa-633 binding to GPR30-GFP or ER-GFP expressing cells, the cells are washed once with PBS and analyzed on FACS Calibur using Cell Quest. Nonspecific binding is determined in presence of 1 μM 17β-estradiol. Competition binding is carried out in the presence of the appropriate concentration of compound that is pre-incubated with the cells for 10 min prior to permeabilization.

The first compound presented below was synthesized using the following scheme:

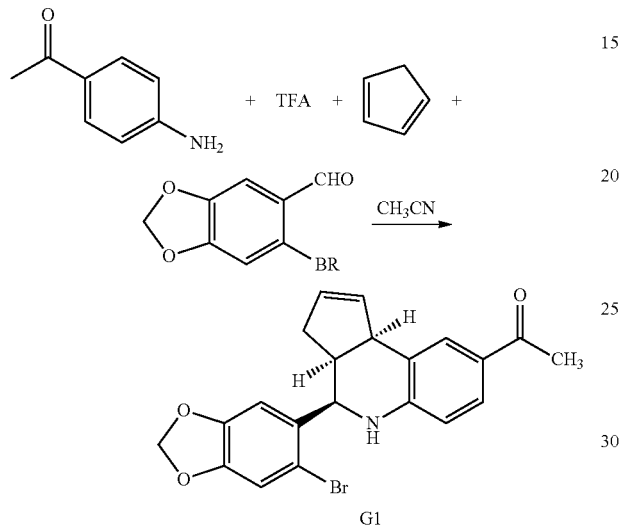

TFA (1.52 g) was added dropwise to a solution of p-aminoacetophenone (2.0 g) in acetonitrile. Freshly distilled cyclopentadiene (3.91 g) was added followed by the bromosubstiuted aldehyde (3.39 g). The mixture was stirred overnight at room temperature and the product was isolated from an aliquot of the mixture by preparative HPLC (acetonitrile in water gradient, 0.05/TFA).

Results

The following compound was found to exhibit selective binding to GPR30 (and not estrogen receptor alpha or beta). The Ki was in the 10$^{-8}$ M range. This compound activates multiple activities of GPR30 in the nM range.

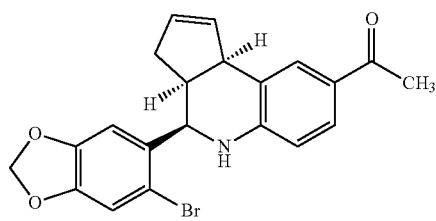 [SMILES: CC(=O)c1ccc2c(c1)[C@@H]1C=CC[C@@H]1[C@H](c1cc3c(cc1Br)OCO3)N2]

The following two compounds were found to exhibit selective binding to estrogen receptor alpha (and not to GPR30). The Ki values were in the 10$^{-9}$-10$^{-8}$ M range. Both of these compounds fail to activate rapid estrogen receptor alpha/beta signaling, block rapid estrogen signaling through estrogen receptor alpha/beta and therefore function as antagonists of rapid signaling.

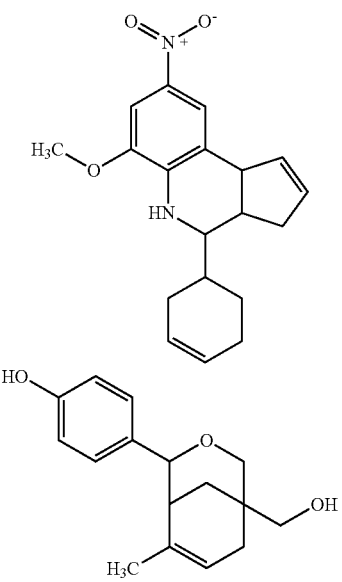

Based upon the above, attempts were made to derivatize the basic compounds presented above to produce compounds according to the present invention.

Examples

Chemical Synthesis of Compounds 4-(6-Bromo-benzo[1,3]dioxol-5-yl)-3a,4,5,9b-tetrahydro-3H-cyclopenta[c]quinoline A solution of the catalyst Sc(OTf)$_3$ (0.0216 g, 0.043 mmol, 10 mol %) in anhydrous acetonitrile (0.2 mL) was added to the mixture of 6-bromopiperanal (0.1 g, 0.43 mmol), aniline (0.041 g, 0.43 mmol) and cyclopentadiene (0.142 g, 2.15 mmol) in acetonitrile (3 mL). The reaction was stirred at ambient temperature (~23° C.) for 1.45 h. The reaction mixture was worked up by removal of solvent and other volatiles by evaporation under reduced pressure. The concentrate was purified by preparative column chromatography using silica gel (SiO$_2$) eluted with 5% EtOAc/Hexanes to give the product as a colorless solid (0.156 g, 98%)

$^1$H NMR (400 MHz, CDCl$_3$): Mixture of syn: anti isomers (9:1) δ 7.16 (s, 1H), 7.05-7.02 (m, 1H), 7.01 (s, 1H), 6.99-6.94 (m, 1H), 6.77-6.73 (m, 1H), 6.60 (dd, J$_1$=2 Hz, J$_2$=8 Hz, 1H), 5.97 (d, J=1.6 Hz, 1H), 5.96 (d, J=1.6 Hz, 1H), 5.86-5.84 (m, 1H), 5.73-5.71 (m, 1H) 5.65-5.64 (m, 1H), 4.88 (d, J=3 Hz, 1H), 4.10 (d, J=8.2 Hz, 1H), 3.5 (bs, 1H), 3.21-3.13 (m, 1H), 2.61-2.54 (m, 1H), 1.82-1.78 (m, 1H).

The minor anti isomer exhibits distinct $^1$H NMR signals at 6.58-6.55 (dd, J$_1$=2 Hz, J$_2$=8 Hz, 1H), 6.06-6.03 (m, 2H minor), 5.74-5.72 (m, 1H), 3.94-4.01 (m, 1H).

$^{13}$C NMR (50 MHz, CDCl$_3$): δ 147.51, 147.25, 145.34, 134.61, 134.00, 130.22, 128.98, 126.28, 126.14, 119.41, 116.07, 113.05, 112.85, 108.08, 101.72, 56.72, 46.08, 42.22, 31.37.

The minor anti isomer exhibits distinct $^{13}$C NMR signals at 135.91, 129.41, 128.27, 121.07, 118.67, 114.95, 112.23, 109.08, 100.35, 89.02, 77.10, 55.69, 48.31, 46.80, 43.50, 35.54, 22.44.

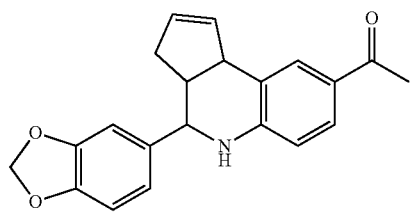 [SMILES: CC(=O)c1ccc2c(c1)C1C=CCC1C(c1ccc3c(c1)OCO3)N2]

1-(4-Benzo[1,3]dioxol-5-yl-3a,4,5,9b-tetrahydro-3H-cyclopenta[c]quinolin-8-yl)-ethanone A solution of Sc(OTf)$_3$ (0.0246 g, 0.5 mmol, 10 mol %) in acetonitrile (0.2 mL) was added to the mixture of piperanal (0.075 g, 0.5 mmol), p-aminoacetophenone (0.0 67 g, 0.5 mmol) and cyclopentadiene (0.165 g, 2.5 mmol) in acetonitrile (3 mL). The reaction was stirred at ambient temperature (~23° C.) for 2 h. The reaction mixture was concentrated in vacuo. The crude material was purified by preparative column chromatography using silica gel (SiO$_2$) eluted with 15% EtOAc/Hexane to give the product as a colorless solid (0.135 g, 81%).

$^1$H NMR (400 MHz, CDCl$_3$): δ 7.69 (s, 1H), 7.61 (dd, J$_1$=1.56 Hz, J$_2$=8.3 Hz, 1H), 6.90 (s, 1H), 6.87 (d, J=8 Hz, 1H), 6.81 (d, J=8 Hz, 1H), 6.59 (d, J=8.4 Hz, 1H), 5.97 (s, 2H), 5.94-5.90 (m, 1H), 5.69-5.65 (m, 1H), 4.63 (d, J=3 Hz, 1H), 4.18 (s, 1H), 4.12-4.07 (m, 1H), 3.0-2.92 (m, 1H), 2.6-2.52 (m, 1H), 2.50 (s, 3H), 1.90-1.84 (m, 1H).

$^{13}$C NMR (100 MHz, CDCl$_3$): δ 196.52, 150.08, 147.83, 146.83, 135.83, 133.77, 130.52, 130.04, 128.41, 127.76, 124.93, 119.40, 114.89, 108.27, 106.85, 101.05, 57.15, 45.99, 45.61, 31.45, 26.03.

The minor anti isomer exhibits distinct $^{13}$C NMR signals at δ 149.84, 136.07, 128.41, 127.12, 123.69, 122.01, 115.32, 113.38, 108.01, 101.11, 46.53, 42.67, 35.66, 25.23, 22.60, 14.08.

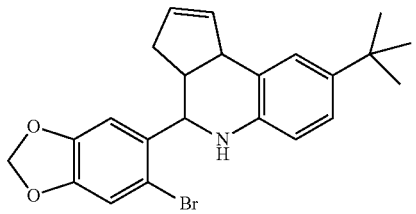 [SMILES: CC(C)(C)c1ccc2c(c1)C1C=CCC1C(c1cc3c(cc1Br)OCO3)N2]

4-(6-Bromo-benzo[1,3]dioxol-5-yl)-8-tert-butyl-3a,4,5,9b-tetrahydro-3H-cyclopental[c]quinoline A solution of Sc(OTf)$_3$ (0.0113 g, 0.023 mmol, 10 mol %) in acetonitrile (0.1 mL) was added to the mixture of 6-bromopiperanal (0.0535 g, 0.023 mmol), p-tent-butylaniline (0.0345 g, 0.23 mmol) and cyclopentadiene (0.076 g, 1.15 mmol) in acetonitrile (3 mL). The reaction was stirred at rt for 4 h. The solvents were evaporated under reduced pressure. The crude material was purified by preparative column chromatography using silica gel (SiO$_2$) eluted with 10% EtOAc/hexane to give the product as a colorless solid (0.096 g, 98%). The structural identity and purity were characterized by spectroscopic methods ($^1$H and $^{13}$C NMR).

$^1$H NMR (200 MHz, CDCl$_3$): δ 7.22 (s, 1H), 7.06 (m, 1H), 7.04 (s, 1H), 7.02-7.00 (m, 1H), 6.58 (d, J=8 Hz, 1H), 5.99 (d, J=1.5 Hz, 1H), 5.98 (d, J=1.5 Hz, 1H), 5.88-5.86 (m, 1H), 5.68-5.64 (m, 1H), 4.89 (d, J=3 Hz, 1H), 4.11 (dd, J$_1$=2.2 Hz, J$_2$=7.7 Hz, 1H), 3.25-3.11 (m, 1H), 2.59-2.53 (m, 1H), 1.82-1.76 (m, 1H), 1.28 (s, 9H).

$^{13}$C NMR (50 MHz, CDCl$_3$): δ 147.49, 147.22, 142.82, 142.21, 134.81, 134.13, 130.22, 125.58, 125.53, 123.39, 115.79, 113.07, 112.83, 108.17, 101.71, 56.81, 46.34, 42.28, 34.00, 31.56, 31.36.

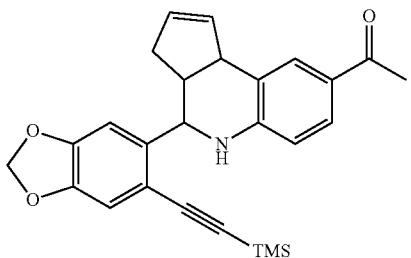 [SMILES: CC(=O)c1ccc2c(c1)C1C=CCC1C(c1cc3c(cc1C#C[Si](C)(C)C)OCO3)N2]

1-[4-(6-Trimethylsilanylethynyl-benzo[1,3]dioxol-5-yl)-3a,4,5,9b-tetrahydro-3H-cyclopenta[c]quinolin-8-yl]-ethanone A solution of the catalyst Sc(OTf)$_3$ (0.032 g, 0.065 mmol, 10 mol %) in acetonitrile (0.2 mL) was added to the mixture of 6-trimethylsilanylethynyl-benzo[1,3]dioxole-5-carbaldehyde (0.160 g, 0.65 mmol), p-aminoacetophenone (0.0878 g, 0.65 mmol) and cyclopentadiene (0.214 g, 3.25 mmol) in acetonitrile (3 mL). The reaction was stirred at ambient temperature (~23° C.) and the progress was monitored by thin layer chromatography. The reaction was complete after 2 hr. The reaction mixture was worked up by removal of solvent and other volatiles by evaporation under reduced pressure. The crude material was purified by preparative column chromatography using silica gel (SiO$_2$) eluted with EtOAc/hexane (polar phase composition 8% EtOAc). The fractions containing pure product were evaporated in vacuo. The yield was 97%.

$^1$H NMR (400 MHz, CDCl3): δ 7.70 (s, 1H), 7.60 (dd, J$_1$=2 Hz, J$_2$=8.4 Hz, 1H), 7.05 (s, 0.2H), 7.04 (s, 1H), 6.93 (s, 0.2H), 6.91 (s, 1H), 6.63 (d, J=8.4 Hz, 1H), 5.96-5.93 (m, 3H), 5.67-5.63 (m, 1H), 5.13 (d, J=3 Hz, 1H), 4.22 (s, 1H), 4.06 (d, J=8.1 Hz, 1H), 3.9 (bs, 0.2H), 3.27-3.19 (m, 1H), 2.50-2.49 (m, 1H), 2.48 (s, 3H), 2.46-2.43 (m, 1H), 1.82-1.74 (m, 1H), 0.023 (s, 9H).

The minor anti isomer exhibits distinct $^1$H NMR signals at 6.55 (d, J=8.4 Hz, 1H), 5.74-5.71 (m, 1H), $^{13}$C NMR (100 MHz, CDCl$_3$): δ 196.32, 150.15, 148.41, 146.10, 139.29, 133.78, 130.40, 129.98, 128.38, 127.56, 124.97, 115.05, 114.24, 111.89, 106.08, 102.32, 101.40, 98.53, 54.78, 45.50, 42.81, 31.34, 25.86, 0.12.

The minor anti isomer exhibits distinct $^{13}$C NMR signals at δ 149.83, 148.66, 146.63, 139.30, 135.56, 128.73, 127.92, 122.44, 116.57, 113.65, 111.30, 107.15, 102.63, 97.68, 53.52, 46.36, 43.09, 36.55, 35.32, 34.53, 28.91, 22.49, 13.97.

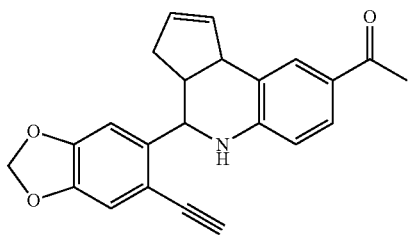 [SMILES: C#Cc1cc2c(cc1C1Nc3ccc(C(C)=O)cc3C3C=CCC31)OCO2]

1-[4-(6-Ethynyl-benzo[1,3]dioxol-5-yl)-3a,4,5,9b-tetrahydro-3H-cyclopenta[c]quinolin-8-yl]-ethanone Potassium carbonate (0.058 g, 0.42 mmol) was added to the 1-[4-(6-trimethylsilanylethynyl-benzo[1,3]dioxol-5-yl)-3a,4,5,9b-tetrahydro-3H-cyclopenta[c]quinoline-8-yl]-ethanone (0.090 g, 0.21 mmol) in methanol (4 mL) and stirred for 2 hr. The reaction mixture poured into water (25 mL) and the product was extracted with chloroform (3×5 mL), dried over anhydrous sodium sulfate and concentrated in vacuo. The crude material was purified by silica gel column chromatography using 10% EtOAc/Hexanes to give the product as a colorless solid (0.056 g, 75%)

$^1$H NMR (200 MHz, CDCl$_3$): δ 7.70 (s, 1H), 7.61 (dd, J$_1$=1.2 Hz, J$_2$=8.4 Hz, 1H), 7.07 (s, 1H), 6.97 (s, 1H), 6.6 (d, J=8 Hz, 1H), 6.00 (m, 1H), 5.95-5.92 (m, 1H), 5.68-5.66 (m, 1H), 5.16 (d, J=3.5 Hz, 1H), 4.13-4.06 (m, 2H), 3.25 (s, 1H), 3.24-3.13 (m, 1H), 2.59-2.52 (m, 1H), 2.50 (s, 3H), 1.89-1.84 (m, 1H).

$^{13}$C NMR (50 MHz, CDCl3): δ 196.47, 150.15, 148.76, 146.36, 139.47, 133.83, 130.49, 130.09, 128.69, 127.68, 125.22, 115.14, 113.37, 112.54, 106.31, 101.60, 81.19, 81.04, 54.89, 45.67, 43.19, 31.49, 26.03.

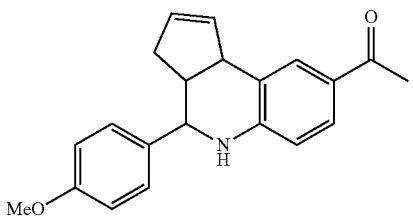 [SMILES: COc1ccc(C2Nc3ccc(C(C)=O)cc3C3C=CCC32)cc1]

1-[4-(4-Methoxy-phenyl)-3a,4,5,9b-tetrahydro-3H-cyclopenta[c]quinolin-8-yl]-ethanone 4-Methoxybenzaldehyde (0.074 g, 0.5 mmol) and 4-aminoacetophenone (0.068 g 0.5 mmol) were heated to melting in a round bottom flask, then a solution of the catalyst Sc(OTf)$_3$ (0.0248 g, 0.05 mmol, 10 mol %) in anhydrous acetonitrile (0.2 mL) was added to the molten solid, followed by a solution of cyclopentadiene (0.165 g, 2.5 mmol) in acetonitrile (3 mL). The reaction was stirred at rt for 2.30 h. The reaction mixture was concentrated under reduced pressure. The crude material was purified by preparative column chromatography using silica gel (SiO$_2$) eluted with 10% EtOAc/Hexanes to give the product as a colorless solid (0.120 g, 76%).

NMR (200 MHz, CDCl$_3$): δ 7.69 (s, 1H), 7.61 (dd, J$_1$=1.8 Hz, J$_2$=8.2, 1H), 7.37 (d, J=4 Hz, 2H), 6.94 (d, J=3 Hz, 2H), 6.93 (d, J=3 Hz, 1H), 5.93-5.90 (m, 1H), 5.67-5.64 (m, 1H), 4.66 (d, J=3 Hz, 1H), 4.20 (s, 1H), 4.13-4.08 (m, 1H), 3.8 (s, 3H), 3.00-2.95 (m, 1H), 2.52 (s, 3H), 1.90-1.82 (m, 1H).

$^{13}$C NMR (50 MHz, CDCl$_3$): δ 196.42, 159.04, 150.30, 133.96, 133.86, 13.54, 130.08, 128.46, 127.75, 127.65, 125.03, 114.86, 114.02, 56.95, 55.30, 46.03, 45.75, 31.52, 26.01.

The minor anti isomer exhibits distinct $^{13}$C NMR signals at δ 149.97, 136.10, 128.46, 128.35, 128.05, 128.75, 127.24, 113.81, 113.67, 77.18, 46.62, 42.72, 35.78.

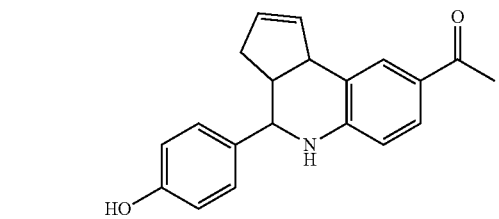 [SMILES: CC(=O)c1ccc2c(c1)C1C=CCC1C(c1ccc(O)cc1)N2]

1-[4-(4-Hydroxy-phenyl)-3a,4,5,9b-tetrahydro-3H-cyclopenta[c]quinolin-8-yl]-ethanone 4-Hydroxybenzaldehyde (0.061 g, 0.5 mmol) and 4-Aminoacetophenone (0.0675 g, 0.5 mmol) were refluxed in toluene for 16 h to form the imine. The solvents were evaporated under reduced pressure. A solution of the catalyst Sc(OTf)$_3$ (0.0246 g, 0.05 mmol, 10 mol %) in acetonitrile (0.2 mL) was added to a mixture of imine and cyclopentadiene (0.165 g, 2.5 mmol) in acetonitrile (3 mL). The reaction was stirred at rt for 15 h. The reaction mixture was concentrated under reduced pressure. The crude material was purified by recrystralization from hot chloroform to give the product as a colorless solid (0.114 g, 75%)

$^1$H NMR (400 MHz, CD$_3$OCD$_3$): Mixture of syn: anti isomers (9.25:0.75) δ 8.31 (d, J=1.2 Hz, 1H), 7.58 (d, J=8.4 Hz, 1H), 7.26 (d, J=8.4 Hz, 2H), 6.83 (d, J=9 Hz, 2H), 6.8 (s, 1H), 5.97-5.94 (m, 1H), 5.61-5.60 (m, 1H), 5.54 (s, 1H) 4.63 (d, J=3 Hz, 1H), 4.09 (d, J=8.6 Hz, 1H), 2.99-2.94 (m, 2H), 2.53-2.47 (m, 1H), 2.42 (s, 3H), 1.77-1.73 (m, 1H).

The minor anti isomer exhibits distinct $^1$H NMR signals at 7.74 (d, J=8.4 Hz, 11-1), 7.21 (d, J=8.4 Hz, 1H), 6.66 (d, J=9 Hz, 1H), 4.31 (d, J=5.6 Hz, 1H).

$^{13}$C NMR (100 MHz, CD$_3$OCD$_3$): δ 195.78, 157.44, 152.02, 135.33, 133.94, 130.81, 130.63, 128.75, 128.40, 128.03, 125.32, 115.97, 115.78, 57.34, 47.15, 46.52, 32.28, 26.03.

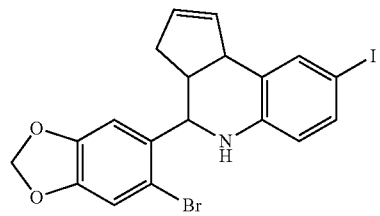 [SMILES: Brc1cc2c(cc1C1Nc3ccc(I)cc3C3C=CCC31)OCO2]

4-(6-Bromo-benzo[1,3]dioxol-5-yl)-8-iodo-3a,4,5,9b-tetrahydro-3cyclopenta[c]quinoline A solution of the catalyst Sc(OTf)$_3$ (4.7 mg, 0.009 mmol, 10 mol %) in anhydrous acetonitrile (0.1 mL) was added to the mixture of 6-bromopiperanal (0.022 g, 0.096 mmol), p-aminoacetophenone (0.021 g, 0.096 mmol) and cyclopentadiene (0.032 g, 0.48 mmol) in acetonitrile (0.5 mL). The reaction mixture was stirred at rt for 2.30 h. The solvent was evaporated under reduced pressure. The crude material was purified by silica gel column chromatography using 10% EtOAc/Hexanes to give the product as a colorless solid (0.041 g, 86%).

$^1$H NMR (400 MHz, CDCl$_3$): Mixture of syn: anti isomers (8.3:1.7) δ 7.33 (s, 1H), 7.24 (dd, J$_1$=2 Hz, J$_2$=8.4 Hz, 1H), 7.17 (s, 1H), 7.02 (s, 1H), 6.39 (d, J=8.4 Hz, 1H), 6.00 (d, J=1.4 Hz, 1H), 5.98 (d, J=1.4 Hz, 1H), 5.84-5.81 (m, 1H), 5.69-5.66 (m, 1H), 4.86 (d, J=3 Hz, 1H), 4.05 (d, J=8.5, 1H), 3.55 (s, 1H), 3.19-3.11 (m, 1H), 2.57-2.50 (m, 1H), 1.83-1.76 (m, 1H).

The minor anti isomer exhibits distinct $^1$H NMR signals at δ 7.51 (s, 1H), 6.80-6.77 (m, 2H), 6.07-6.04 (m, 2H), 5.90-5.85 (m, 1H), 5.77-5.71 (m, 1H), 4.87-4.85 (m, 1H), 4.29-4.18 (m, 1H).

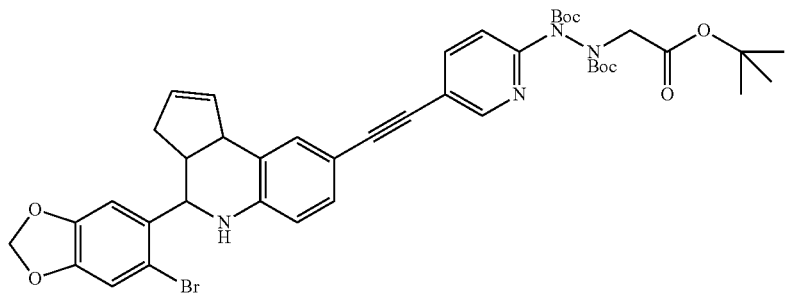 [SMILES: CC(C)(C)OC(=O)CN(C(=O)OC(C)(C)C)N(C(=O)OC(C)(C)C)c1ccc(C#Cc2ccc3c(c2)C2C=CCC2C(c2cc4c(cc2Br)OCO4)N3)cn1]

(N'-{5-[4-(6-Bromo-benzo[1,3]dioxol-5-yl)-3a,4,5,
9b-tetrahydro-3H-cyclopenta[c]quinolin-8-ylethy-
nyl]-pyridin-2-yl}-N,N-bis-tertbutyloxycarbonyl-
hydrazino)-acetic acid-tert-butyl ester The aryl iodide (4-(6-Bromo-benzo[1,3]dioxol-5-yl)-8-iodo-3a,4,5,9b-tetrahydro-3cyclopenta[c]quinoline) (0.084 g, 0.17 mmol), was combined with the pyridyl alkyne (0.076 g, 0.17 mmol), dichlorobis(triphenylphosphine) palladium (II) (0.0019 g, 1.6 mol %) and copper iodide (0.001 g, 3 mol %) in a 10 mL round bottom flask, under an argon atmosphere. Dry triethylamine (1.5 mL) was added and allowed to stir rt under argon for 2 h. The reaction mixture was evaporated under vaccum. The crude material was purified by silica gel column chromotography 25% EtOAc/Hexanes to give the product as a white solid (0.103 g, 75%).

$^1$H NMR (400 MHz, CDCl$_3$): Mixture of syn: anti isomers (8.7:1.3) δ 8.47 (d, J=1.6 Hz, 1H), 7.77-7.23 (m, 1H), 7.60-7.56 (m, 1H), 7.27-7.26 (m, 1H), 7.17-7.13 (m, 2H), 7.03 (s, 1H), 6.59-6.52 (m, 1H), 6.00-5.98 (m, 2H), 5.92-5.87 (m, 1H), 5.69-5.66 (m, 1H), 4.93 (bs, 1H), 4.32-4.28 (m, 1H), 4.1-4.05 (m, 2H), 3.99-3.94 (m, 1H), 3.75 (bs, 1H), 3.21-3.14 (m, 1H), 2.52-2.50 (m, 1H), 1.8-1.78 (m, 1H), 1.5-1.39 (m, 27H).

The minor anti isomer exhibits distinct $^1$H NMR signals at 7.42 (s, 1H), 6.85-6.79 (m, 1H), 6.07-6.04 (m, 2H), 5.95-5.92 (m, 1H), 5.77-5.74 (m, 1H), 5.01 (bs, 0.15H), 3.47 (d, J=4.5 Hz, 1H), 2.67-2.62 (m, 1H), 2.14-2.09 (m, 1H)

(N'-{5-[4-(6-Bromo-benzo[1,3]dioxol-5-yl)-3a,4,5,
9b-tetrahydro-3H-cyclopenta[c]quinolin-8-ylethy-
nyl]-pyridin-2-yl}-hydrazino)-acetic acid The (N'-{5-[4-(6-Bromo-benzo[1,3]dioxol-5-yl)-3a,4,5,9b-tetrahydro-3H-cyclopenta[c]quinolin-8-ylethynyl]-pyridin-2-yl}-N,N-bis-tertbutyloxycarbonyl-hydrazino)-acetic acid-tert-butyl ester (0.080 g, 0.098 mmol) was dissolved in dichloromethane (0.5 mL). Trifluoroacetic acid (0.5 mL) was added dropwise and the solution was allowed to stir at room temperature for 0.45 h. The mixture was diluted with dichloromethane (4 mL), and the excess TFA was neutralized with cold, saturated NaHCO$_3$ (4 mL). The organic layer was dried over anhydrous Na$_2$SO$_4$ and concentrated under reduced pressure. The crude material was purified by silica gel column chromatography (15% MeOH/DCM) to give the product as a colorless solid (0.0495 g, 92%).

$^1$H NMR (400 MHz, CD$_3$OD): δ 7.93-7.92 (m, 1H), 7.82 (dd, J$_1$=2 Hz, J$_2$=9 Hz, 1H), 7.77-7.76 (m, 1H), 7.68 (dd, J$_1$=2 Hz, J$_2$=8.7 Hz, 1H), 7.11 (s, 1H), 7.07 (s, 1H), 7.01 (d, J=9 Hz, 1H), 6.75 (d, J=9 Hz, 1H), 5.64 (d, J=4.5 Hz, 1H), 4.94 (d, J=3 Hz, 1H), 4.28 (s, 2H), 4.08 (d, J=9 Hz, 1H), 3.67 (s, 2H), 3.21-3.13 (m, 1H), 2.51-2.44 (m, 1H), 1.76-1.69 (m, 1H).

The minor anti isomer exhibits distinct $^1$H-NMR signals at 7.73-7.72 (m, 1H), 7.05 (s, 1H), 6.97 (s, 1H), 6.67 (d, J=9 Hz, 2H), 6.85 (d, J=8.4 Hz, H), 4.34 (d, J=9.1 Hz, 2H), 2.64-2.57 (m, 1H).

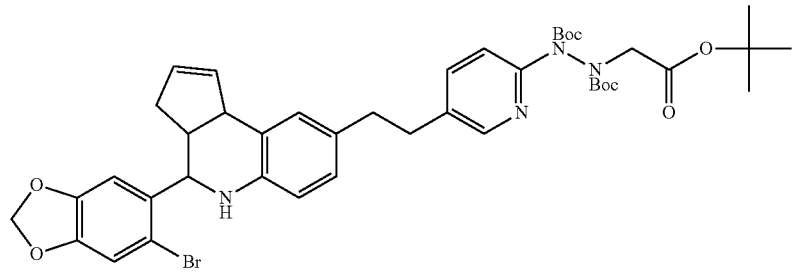

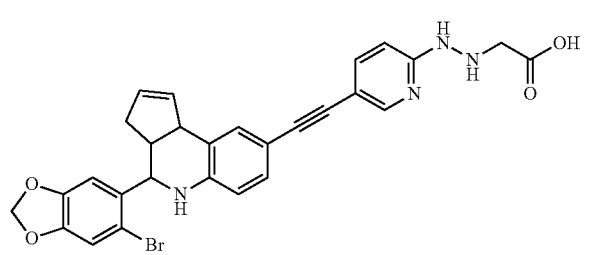 [SMILES: O=C(O)CNNc1ccc(C#Cc2ccc3c(c2)C2C=CCC2C(c2cc4c(cc2Br)OCO4)N3)cn1]

[N'-(5-{2-[4-(6-Bromo-benzo[1,3]dioxol-5-yl)-3a,4,
5,9b-tetrahydro-3H-cyclopenta[c]quinolin-8-yl]-
ethyl}-pyridin-2-yl)-N,N-bis-tertbutyloxycarbonyl
hydrazino]-acetic acid-tert-butyl ester Potassium hydrogen sulfate (0.016 g, 0.11 mmol, 50 mol %) was added to the imine and cyclopentadiene (0.073 g, 1.1 mmol) in methanol (4 mL). The reaction was stirred at rt (~23° C.) for 20 h. The reaction mixture evaporated under reduced pressure. The crude material was purified by silica gel column chromatography using 20% EtOAc/Hexanes to give the product as a colorless solid (0.13 g, 72%).

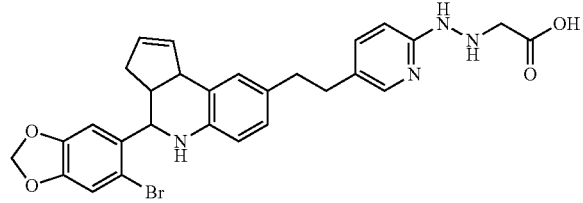 [SMILES: O=C(O)CNNc1ccc(CCc2ccc3c(c2)C2C=CCC2C(c2cc4c(cc2Br)OCO4)N3)cn1]

[N'-(5-{2-[4-(6-Bromo-benzo[1,3]dioxol-5-yl)-3a,4, 5,9b-tetrahydro-3H-cyclopenta[c]quinolin-8-yl]-ethyl}-pyridin-2-yl)-hydrazino]-acetic acid The [N'-(5-{2-[4-(6-Bromo-benzo[1,3]dioxol-5-yl)-3a,4, 5,9b-tetrahydro-3H-cyclopenta[c]quinolin-8-yl]-ethyl}-pyridin-2-yl)-N,N-bis-tertbutyloxycarbonyl hydrazino]-acetic acid-tert-butyl ester (0.050 g, 0.06 mmol) was dissolved in dichloromethane (0.5 mL). Trifluoroacetic acid (0.5 mL) was added dropwise and the solution was allowed to stir at room temperature for 45 min. The mixture was diluted with dichloromethane (4 mL), and the excess TFA was neutralized with cold, saturated NaHCO$_3$ (4 mL). The organic layer was dried over anhydrous Na$_2$SO$_4$ and concentrated under reduced pressure. The crude material was purified by silica gel column chromatography (10% MeOH/DCM) to give the product as a colorless solid (0.031 g, 91%).

$^1$H NMR (400 MHz, CD$_3$OD): Mixture of syn: anti isomers (9:1) δ 7.57 (d, J=9 Hz, 1H), 7.3 (s, 1H), 7.05 (s, 1H), 6.94 (s, 1H), 6.83 (d, J=9 Hz, 1H), 6.63-6.60 (m, 2H), 6.51 (d, J=8 Hz, 1H), 5.89 (d, J=1.2 Hz, 1H), 5.87 (d, J=1.2 Hz, 1H), 5.67-5.63 (m, 1), 4.64 (d, J=3.2 Hz, 1H), 3.85 (d, J=8.2 Hz, 1H), 3.48 (s, 2H), 3.09-3.00 (m, 1H), 2.7-2.65 (m, 4H), 1.62-1.55 (m, 1H).

The minor anti isomer exhibits distinct $^1$H-NMR signals at 6.92 (d, J=5.5 Hz, 1H), 6.72 (d, J=8.2 Hz, 1H), 5.99-5.97 (m, 2H), 5.72-5.69 (m, 1H), 5.60-5.56 (m, 1H), 5.52-5.49 (m, 1H).

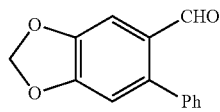 [SMILES: O=Cc1cc2c(cc1-c1ccccc1)OCO2]

6-Phenyl-benzo[1,3]dioxole-5-carbaldehyde

To a mixture of 6-bromopiperanal (0.115 g, 05 mmol), phenylboronic acid (0.072 g, 06 mmol), palladium acetate (0.0056 g, 0.025 mmol, 5 mol %) and TPPTS (0.042 g, 0.75 mmol, 15 mol %) in acetonitrile:water (1.5 mL: 0.5 mL) was added disiopropylamine (0.253 g, 1.25 mmol) and allowed to stir at 80° C. for 30 min. The reaction mixture was diluted with water (25 mL) and extracted using dichloromethane (3×5 mL), dried over anhydrous sodium sulfate and concentrated under reduced pressure. The crude material was purified by preparative silica gel column chromatography using 8% EtOAc/Hex and gave the product as a white solid (0.097 g, 85%).

$^1$H NMR (400 MHz, CDCl$_3$): δ 9.7 (s, 1H), 7.47 (s, 1H), 7.46-7.41 (m, 3H), 7.37-7.31 (m, 2H), 6.85 (s, 1H).

$^{13}$C NMR (50 MHz, CDCl$_3$): δ 190.55, 152.02, 147.75, 143.60, 137.53, 130.08, 128.81, 128.32, 128.07, 110.19, 106.23, 102.04

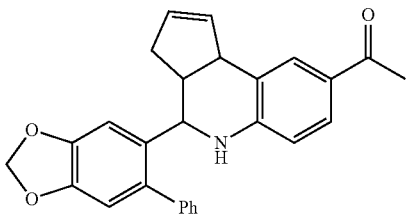 [SMILES: CC(=O)c1ccc2c(c1)C1C=CCC1C(c1cc3c(cc1-c1ccccc1)OCO3)N2]

1-[4-(6-Phenyl-benzo[1,3]dioxol-5-yl)-3a,4,5,9b-tetrahydro-3H-cyclopenta[c]quinolin-8-yl]-ethanone To a mixture of 6-phenylpiperanal (0.050 g, 0.22 mmol) and 4-aminoacetophenone (0.030 g, 0.22 mmol), in acetonitrile (1.5 mL) was added cyclopentadiene (0.2 mL) and then a solution of Sc(OTf)$_3$ (0.0098 g, 0.02 mmol) in acetonitrile (0.6 mL). The reaction was allowed to stir at rt for 16 h. The reaction mixture was concentrated under reduced pressure. The crude material was purified by preparative silica gel column chromatography using 5% EtOAc/Hexanes to give the product as a white solid (0.062 g, 70%).

$^1$H NMR (400 MHz, CDCl$_3$): Mixture of syn: anti isomers (2:1): δ 7.57 (s, 2H), 7.55 (d, J=2.0 Hz, 1H), 7.38-7.25 (m, 9H), 7.24-7.21 (m, 8H), 7.18-7.16 (m, 5H), 6.7 (s, 1H), 6.69 (s, 2H), 6.54-6.51 (m, 3H), 6.00-5.99 (m, 7H), 5.88-5.80 (m, 2.5H), 5.50-5.65 (m, 4H), 4.66 (d, J=3.0 Hz, 2.5H), 4.07 (s, 2.5H), 3.92 (d, J=10.0 Hz, 2H), 3.75 (d, J=7.4 Hz, 2.5 H), 2.77-2.70 (m, 2H), 2.66-2.59 (m, 3.5H, 2.49 (s, 2.5H), 2.45 (s, 5H), 2.37-2.31 (m, 2H), 1.98-1.87 (m, 4H).

The minor anti isomer exhibits distinct $^1$H NMR signals at δ 7.80 (d, J=1.8 Hz, 1H), 7.62 (dd, J$_1$=2.0 Hz, J$_2$=8.4 Hz, 1H), 7.04 (s, 1.5H), 5.38-5.36 (m, 1.5H), 4.37 (s, 1H), $^{13}$C NMR (50 MHz, CDCl$_3$): Mixture of syn: anti isomers (2:1) δ 150.22, 147.09, 146.26, 140.62, 136.02, 133.69, 132.59, 130.65, 130.01, 129.22, 129.18, 128.25, 128.05, 127.64, 127.22, 124.71, 114.79, 110.41, 106.51, 101.21, 53.27, 45.44, 44.38, 31.35, 26.00.

The minor anti isomer exhibits distinct $^{13}$C-NMR signals at δ 149.92, 147.54, 146.76, 140.54, 137.21, 136.56, 135.31, 132.71, 130.57, 128.14, 127.97, 127.29, 126.98, 122.38, 113.56, 109.75, 107.24, 101.27, 77.20, 51.88, 46.58, 43.10, 35.52.

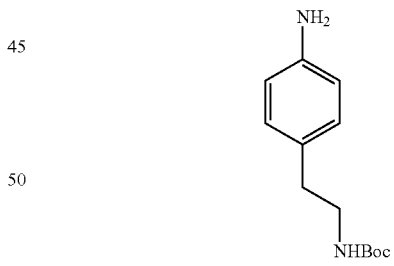

[2-(4-Amino-phenyl)-ethyl]-carbamic acid tert-butyl ester

To a solution of 4-aminophenethylamine (0.136 g, 1 mmol) in dichloromethane (4 mL) at rt was added ($^1$Boc)$_2$(0.218 g, 1 mmol) and allowed to stir for 15 min. The reaction mixture was poured into water and then extracted with dichloromethane (15 mL), the organic layer was dried over anhydrous Na$_2$SO$_4$ and concentrated in vacuo. The crude material was purified by silica gel column chromotography using 15% EtOAc/Hexane to give the product as a colorless solid (0.175 g, 75%)

¹H NMR (400 MHz, CDCl₃): δ 6.97 (d, J=8.4 Hz, 2H), 6.63 (d, J=8.4 Hz, 2H), 4.51 (bs, 1H), 3.59 (s, 2H), 3.32-3.29 (m, 2H), 2.67 (t, J=7.04, 2H), 1.43 (s, 9H).
¹³C NMR (100 MHz, CDCl₃): δ 155.84, 144.77, 129.51, 128.76, 115.28, 79.03, 41.98, 35.26, 28.37.

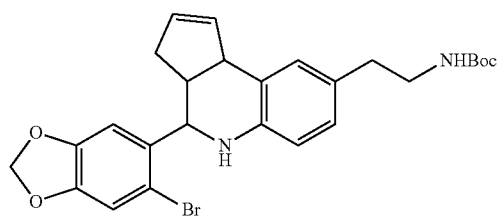 [SMILES: CC(C)(C)OC(=O)NCCc1ccc2c(c1)C1C=CCC1C(c1cc3c(cc1Br)OCO3)N2]

{2-[4-(6-Bromo-benzo[1,3]dioxol-5-yl)-3a,4,5,9b-tetrahydro-3H-cyclopenta[c]quinolin-8-yl]-ethyl}-carbamic acid tert-butyl ester To a mixture of 6-bromopiperanal (0.138 g, 0.6 mmol) and [2-(4-aminophenyl)-ethyl-carbamic acid tert ester (0.141 g, 0.6 mmol) in acetonitrile (4 mL) was added cycopentadiene (0.6 mL). A solution of Sc(OTf)₃ (0.030 g, 06 mmol) in acetonitrile (1 mL) was added to the reaction mixture at rt. After 2 h, the solvents were evaporated in vacuo. The crude reaction mixture was purified by preparative silica gel chromatography using 15-20% EtOAc/Hexanes to give the product as a light yellow solid (0.287 g, 95%).
¹H NMR (400 MHz, CDCl₃): Mixture of syn: anti isomers: (9.25:0.75) δ 7.16 (s, 1H), 7.02 (s, 1H), 6.88 (dd, J₁=1.28 Hz, J₂=7.6 Hz, 1H), 6.57 (d, J=8.0 Hz, 1H), 5.99 (d, J=1.36 Hz, 1H), 5.98 (d, J=1.36 Hz, 1H), 5.87-5.82 (m, 1H), 5.68-5.63 (m, 1H), 4.86 (d, J=3.12 Hz, 1H), 4.56 (bs, 1H), 4.08 (d, J=8.6 Hz, 1H), 3.5 (bs, 1H), 3.37-3.27 (m, 2H), 3.20-3.13 (m, 1H), 2.67 (t, J=6.8 Hz, 2H), 2.62-2.58 (m, 1H), 1.83-1.76 (m, 1H), 1.44 (s, 9H).
The minor, anti isomer exhibits distinct ¹H NMR signals at 7.00 (s, 1H), 6.54 (d, J=8.4 Hz, 1H), 5.92-5.90 (m, 1H), 5.75-5.71 (m, 1H), 4.26 (d, J=10.1 Hz, 1H), 3.96 (bs, 1H).
¹³C NMR (100 MHz, CDCl₃): δ 155.88, 147.48, 147.23, 143.70, 134.54, 133.93, 130.34, 129.70, 126.66, 126.29, 116.27, 113.03, 112.83, 108.07, 79.07, 77.45, 55.77, 46.05, 42.12, 41.94, 35.38, 31.31, 28.41.
The minor anti isomer exhibits distinct ¹³C NMR signals at 136.59, 135.75, 101.72, 35.38, 34.00.

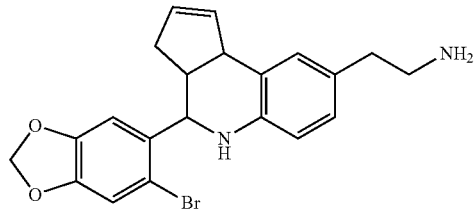 [SMILES: NCCc1ccc2c(c1)C1C=CCC1C(c1cc3c(cc1Br)OCO3)N2]

2-[4-(6-Bromo-benzo[1,3]dioxol-5-yl)-3a,4,5,9b-tetrahydro-3H-cyclopenta[c]quinolin-8-yl]-ethylamine Triflouroacetic acid (1.2 mL) was added dropwise to a solution of {2-[4-(6-bromo-benzo[1,3]dioxol-5-yl)-3a,4,5,9b-tetrahydro-3H-cyclopenta[c]quinolin-8-yl]-ethyl}-carbamic acid tert-butyl ester (0.15 g, 0.3 mmol) in dichloromethane (1.5 mL), and stirred at rt for 1 h. The reaction mixture was diluted with dichloromethane (15 mL) and washed with cold saturated NaHCO₃. Organic layer dried over anhydrous Na₂SO₄ and concentrated under reduced pressure. The crude material was purified by preparative silica gel chromatography using 20% MeOH/DCM and gave the product as a colorless solid (0.115 g, 95%).
¹H NMR (400 MHz, CDCl₃): Mixture of syn: anti isomers (9.1:0.9) δ 7.16 s, 1H), 7.02 (s, 1H), 6.89 (s, 1H), 6.82 (dd, J₁=1.8 Hz, J₂=8.0 Hz, 1H), 6.56 (d, J=8.0 Hz, 1H), 5.99 (d, J=4.0 Hz, 1H), 5.98 (d, J=1.40 Hz, 1H), 5.87-5.83 (m, 1H). 5.66-5.64 (m, 1H), 4.87 (d, J=10.0 Hz, 1H), 4.09 (d, J=8.8 Hz, 1H), 3.47 (bs, 1H), 3.20-3.15 (m, 1H), 3.01-2.91 (m, 1H), 2.67 (t, J=6.8 Hz, 2H), 2.61-2.54 (m, 1H), 2.32-2.24 (bs, 2H), 1.83-1.76 (m, 1H).
The minor anti isomer exhibits distinct ¹H NMR signals at 7.17 (s, 1H), 7.07 (s, 1H), 6.53 (d, J=8.0 Hz, 1H), 5.92-5.90 (m, 1H), 5.74-5.72 (m, 1H), 4.26 (d, J=10.1 Hz, 0.1 H), 3.97-3.94 (m, 0.1H).
¹³C NMR (50 MHz, CDCl₃): Mixture of syn: anti isomers (9.1:0.9) δ 147.40, 147.14, 143.68, 134.51, 133.91, 130.28, 130.18, 129.22, 126.62, 126.18, 116.20, 112.96, 112.76, 108.01, 101.66, 72.12, 56.69, 45.96, 43.04, 42.08, 31.23.
The minor isomer exhibits distinct ¹³C NMR signals at δ 135.69, 128.44, 126.80, 124.07, 115.07, 112.13, 108.73, 107.56, 101.98, 77.19, 63.02, 55.72, 46.72, 43.40, 38.17, 36.70, 35.45.

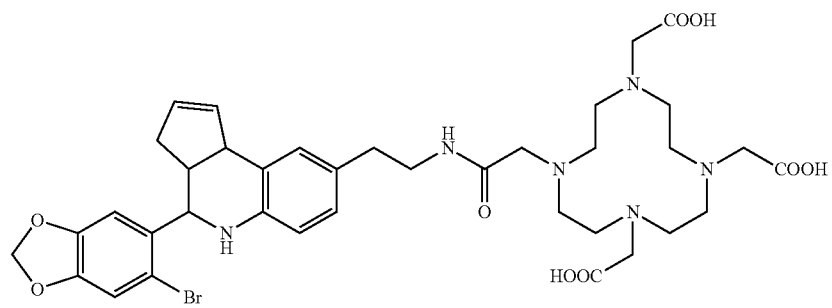 [SMILES: O=C(O)CN1CCN(CC(=O)O)CCN(CC(=O)NCCc2ccc3c(c2)C2C=CCC2C(c2cc4c(cc2Br)OCO4)N3)CCN(CC(=O)O)CC1]

[4-({2-[4-(6-Bromo-benzo[1,3]dioxol-5-yl)-3a,4,5,
9b-tetrahydro-3H-cyclopenta[c]quinolin-8-yl]-ethyl-
carbamoyl}-methyl)-7,10-bis-carboxymethyl-1,4,7,
10tetraaza-cyclododec-1-yl]-acetic acid 2-[4-(6-Bromo-benzo[1,3]dioxol-5-yl)-3a,4,5,9b-tetrahydro-3H-cyclopenta[c]quinolin-8-yl]-ethylamine (0.015 g, 0.036 mmol) and DOTA-N-hydroxysuccinimide ester (0.021 g, 0.041 mmol) were combined with dry dimethylformamide (0.5 mL) and triethylamine (30 µL) under an argon atmosphere and allowed to stir at rt for 12 h. The solvents were evaporated under reduced pressure. The crude material was purified by preparative reverse phase C-18 column chromatography using 60% MeOH/H$_2$O as eluent to give the product as a white solid (0.020, 71%).

$^1$H NMR (400 MHz, CD$_3$OD): δ 7.18 (s, 1H), 7.05 (s, 1H), 6.90 (d, J=1.4 Hz, 1H), 6.81 (dd, J$_1$=1.70 Hz, J$_2$=8.0 Hz, 6.63 (d, J=8.0 Hz, 1H), 5.99 (d, J=1.2 Hz, 1H), 5.97 (d, J=1.2 Hz, 1H), 5.90-5.85 (m, 1H), 5.71-5.68 (m, 0.1H), 5.63-5.58 (m, 1H), 4.74 (d, J=2.9 Hz, 1H), 4.01 (d, J=9.0 Hz, 1H), 3.63-3.56 (m, 4H), 3.45-3.30 (m, 12H), 3.18-3.02 (m, 2H), 3.05-2.80 (m, 10H), 2.70-2.67 (m, 4H), 2.57-2.49 (m, 1H), 1.73-1.67 (m, 1H).

HPLC: Two peaks at retention time of 13.02 and 13.43 min gave the corresponding molecular mass of 802.02 corresponding to the presence of syn and anti diasteromers.

The 2-[4-(6-Bromo-benzo[1,3]dioxol-5-yl)-3a,4,5,9b-tetrahydro-3H-cyclopenta[c]quinolin-8-yl]-ethylamine (2 mg, 0.0048 mmol) in 5 mL rbf, was combined with alexa-546-N-hydroxysuccinimide ester (1 mg) in dry dimethylformamide (0.4 mL) at rt. The mixture was cooled to 0° C., then dry triethylamine (5 µL) was added dropwise and the mixture allowed to stir at rt for 12 h. The reaction mixture was evaporated under reduced pressure. The crude material was purified by preparative reverse phase C-18 chromatography using 20% MeOH/CH$_3$CN to give the product as a red solid.

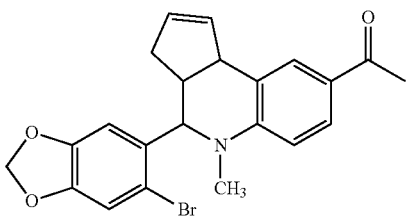

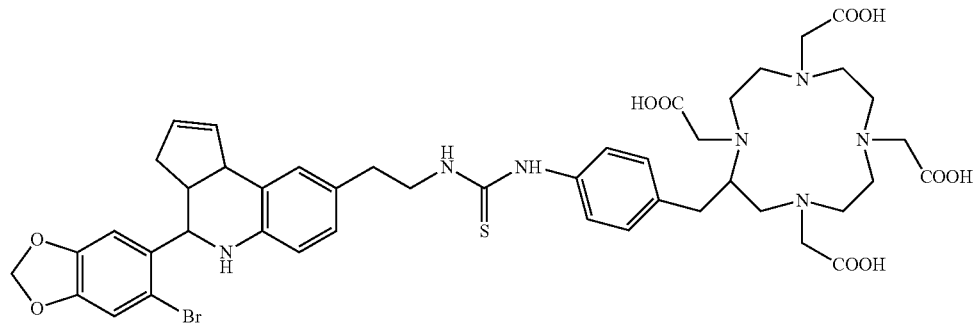 [SMILES: O=C(O)CN1CCN(CC(=O)O)CCN(CC(=O)O)C(Cc2ccc(NC(=S)NCCc3ccc4c(c3)C3C=CCC3C(c3cc5c(cc3Br)OCO5)N4)cc2)CN(CC(=O)O)CC1]

{2-[4-(3-{2-[4-(6-Bromo-benzo[1,3]dioxol-5-yl)-3a,
4,5,9b-tetrahydro-3H-cyclopenta[c]quinolin-8-yl]-
ethyl}-thioureido)-benzyl]-4,7,10-tris-carboxymethyl-1,4,7,10tetraaza-cyclododec-1-yl}-acetic acid 2-[4-(6-Bromo-benzo[1,3]dioxol-5-yl)-3a,4,5,9b-tetrahydro-3H-cyclopenta[c]quinolin-8-yl]-ethylamine (0.015 g, 0.036 mmol) and 4-benzylisothiocyanate-DOTA (0.030 g, 0.044 mmol) were combined with dry dimethylformamide (0.5 mL) and triethylamine (36 µL) under an argon atmosphere and allowed to stir at rt for 12 h. The solvents were evaporated under reduced pressure. The addition of ethanol formed a precipitate of the product, that was isolated by filtration, washed with water and dried to give the product as a colorless solid (0.021 g, 62%).

HPLC-MS: The peaks at retention time of 15.98 min and 16.50 min gave the corresponding molecular mass of 966 which corresponds to the syn and anti diasteromers.

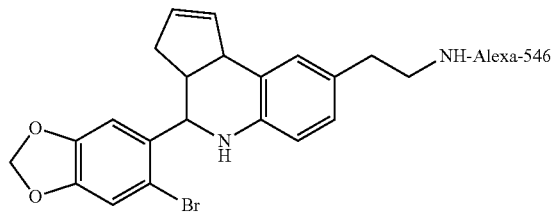

1-[4-(6-Bromo-benzo[1,3]dioxol-5-yl)-5-methyl-3a,
4,5,9b-tetrahydro-3H-cyclopenta[c]quinolin-8yl]-
ethanone C$_{22}$H$_{20}$BrNO$_3$ Exact Mass: 425.06

Mol. Wt.: 426.30

C, 61.98; H, 4.73; Br, 18.74; N, 3.29; O, 11.26

Sodium hydride (0.007 mg, 0.17 mmol) was added cautiously to a solution of 4-(6-bromo-benzo[1,3]dioxol-5-yl)-3a,4,5,9b-tetrahydro-3H-cyclopenta[c]quinolin-8-yl]-ethanone (0.040 g, 0.1 mmol) in dry DMF (0.07 mL) at 0° C. under an argon atmosphere, followed by dropwise addition of methyl iodide (0.020 g, 0.15 mmol). The mixture was allowed to stir for 30 min at 0° C., then warmed to 25° C. for 30 min. The reaction mixture was cooled and cautiously quenched with cold water (1 mL), diluted with water (25 mL) and extracted with EtOAc (3×5 mL), dried over anhydrous sodium sulfate, filtered and concentrated under vacuum. The crude product was purified by silica gel column chromatography using 10% EtOAc/Hexane to give the product as a colorless solid (0.022 g, 53%).

¹H NMR (400 MHz, CDCl₃): Mixture of Syn: Anti isomers (9.5:0.5) δ 7.74-7.72 (m, 2H), 6.98 (s, 1H), 6.70 (d, J=9.16 Hz, 1H), 6.65 (s, 1H), 6.08-6.04 (m, 1H), 5.95 (d, J=1.4 Hz, 1H), 5.94 (d, J=1.4 Hz, 1H), 5.58-5.55 (m, 1H), 4.90 (d, J=5.6 Hz, 1H), 4.0 (d, J=7.6 Hz, 1H), 3.09-3.02 (m, 1H), 2.78 (s, 3H), 2.53 (s, 3H), 2.31-2.25 (m, 1H), 2.10-2.04 (m, 1H).

The minor anti isomer exhibits distinct ¹H NMR signals at δ 7.03 (d, J=7.03 Hz, 1H), 4.12 (d, J=7.0 Hz, 1H), 2.80 (s, 3H), 2.51 (s, 3H).

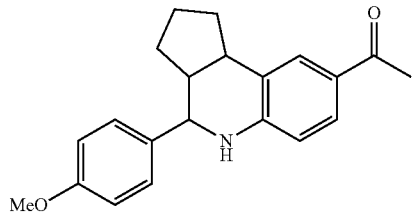 [SMILES: COc1ccc(C2Nc3ccc(C(C)=O)cc3C3CCCC32)cc1]

1-[4-(4-Methoxy-phenyl)-2,3,3a,4,5,9b-hexahydro-1H-cyclopenta[c]quinolin-8-yl]-ethanone $C_{21}H_{23}NO_2$ Exact Mass: 321.17

Mol. Wt.: 321.41

C, 78.47; H, 7.21; N, 4.36; O, 9.96

A mixture of 1-[4-(2-Bromo-4-methoxy-phenyl)-3a,4,5,9b-tetrahydro-3H-cyclopenta[c]quinolin-8-yl]-ethanone and 10% palladium on carbon (11 mg) in ethanol (5 mL) was stirred under an atmosphere of hydrogen for 1 h. The reaction mixture was filtered through silica gel and evaporated under reduced pressure. The crude product was purified by silica gel column chromatography using 5% EtOAc/Hexanes to provide the product as a white solid (0.040 g, 80%).

¹H NMR (400 MHz, CDCl₃): Mixture of Syn: Anti isomers (9.2:0.8) δ 7.80 (s, 1H), 7.62 (dd, $J_1$=2.0 Hz, $J_2$=8.51 Hz, 1H), 7.31 (d, J=8.8 Hz, 2H), 6.90 (d, J=8.8 Hz, 2H), 6.90 (d, J=8.51 Hz, 1H), 4.62 (d, J=3.0 Hz, 1H), 4.30 (bs, 1H), 3.81 (s, 3H), 3.47-3.42 (m, 1H), 2.50 (s, 3H), 2.44-2.41 (m, 1H), 2.17-1.95 (m, 1H), 1.68-1.26 (m, 4H).

The minor anti isomer exhibits distinct ¹H NMR signals at δ 6.97 (d, J=8.80 Hz, 2H), 4.49 (bs, 1H), 3.87 (s, 3H), 2.60 (s, 3H)

¹³C NMR (300 MHz, CDCl₃), δ 196.65, 158.94, 149.61, 134.56, 130.24, 127.92, 127.86, 127.54, 125.18, 113.88, 113.80, 56.55, 55.30, 46.55, 40.30, 34.50, 26.03, 24.01, 23.01.

Biological Characterization of Compounds According to the Present Invention

In order to understand the interactions of novel ligands with GPR30, we determine whether and how such compounds mediate receptor activation through GPR30. Multiple assays, including calcium mobilization, PI3kinase activation, EGFR phosphorylation, transcriptional activation, migration and proliferation are used to assess cellular signaling through GPR30 in response to treatment with estrogen derivatives in order to confirm membrane permeability and determine whether the compounds act as agonists or antagonists. Through these studies, we gain a better understanding of the structure-activity relationships related to GPR30 function and reveal whether compounds display partial or selective agonism, antagonism of SERM-like properties. These results help assist further design of active compounds.

Calcium Mobilization.

Figure 6:
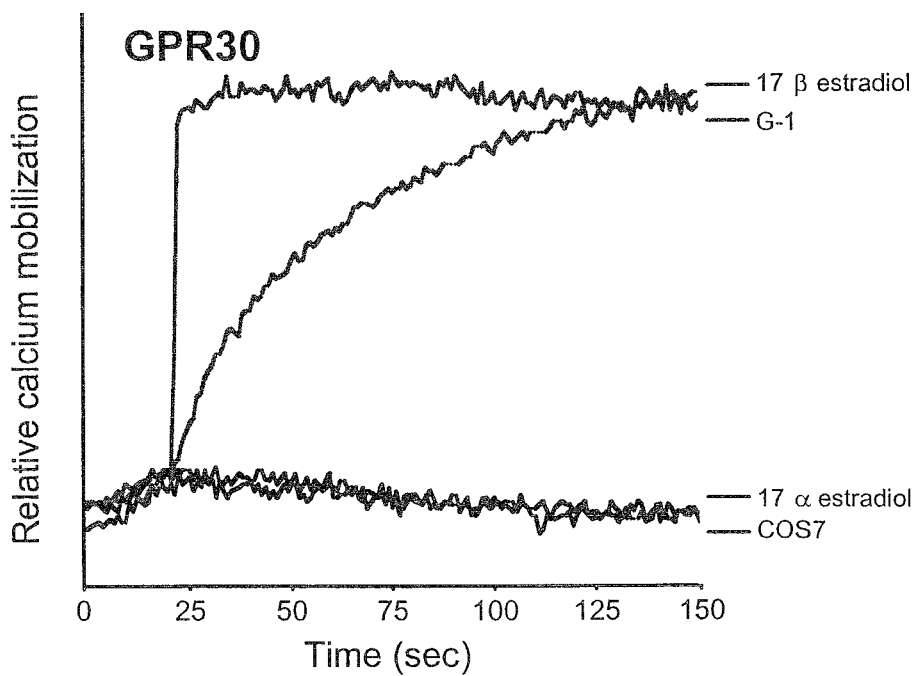
FIG. 6 shows the action of G-1 as an agonist in the mobilization of intracellular calcium by GPR30. The activity of G-1 was compared to that of 17 β-estradiol using indol-AM-loaded COS7 cells transfected with either GPR30-GFP or mock-transfected (COS7, stimulated with 17 β-estradiol). Ligand addition was performed at 20 sec. G-1 and 17 β-estradiol were used at 1 nM; 17β-estradiol was used at 1 µM.

We have demonstrated that cells transfected to express only GPR30 or one of the classical estrogen receptors (ERα or ERβ) respond to estrogen stimulation with rapid calcium mobilization. This assay utilizes real time fluorescence measurements of indol-AM (calcium-sensitive fluorophore) loaded cells providing a real time analysis of receptor function. This approach also allows us to examine the cellular permeability of the compounds (since the screening was carried out in permeabilized cells). For example, in the case of our novel GPR30-specific ligand G-1, we observed that the kinetics of cellular activation were slower than those for estrogen (FIG. 6). This could be due to slower uptake of the ligand in to the cell, slower binding to the receptor as compared to estrogen, or slower activation of the signaling response once bound to the receptor. Nevertheless, the result demonstrates a half time for activation by G-1 of approximately 30 sec, suggesting that in this time frame a significant amount of ligand has entered the cell, bound to the receptor and activated downstream effectors. Such rapid kinetic analyses, along with dose responses, will be important in assessing the cellular permeability of the many compounds to be screened and synthesized. Although equilibrium binding measurements using permeabilized cells will indicate whether a competitor can displace the reporter over time (5-15 min), only this assay can easily and effectively estimate the rapidity (seconds time scale) with which compounds cross the cell membrane.

Kinase Activation.

In addition to calcium mobilization, we have monitored GPR30-mediated activation of multiple kinases including PI3K and EGFR. Activation of these proteins, measured by PH-reporter translocation and anti-phospho-EGFR antibody binding, respectively, occurs on a slower timescale (5-15 min) than calcium mobilization. Nevertheless, these assays represent important tests of receptor function as some compounds may elicit specific activation events through GPR30 to the exclusion of others.

Transcriptional Activation.

Estrogen is best known for its ability to regulate transcription through binding to classical ERs. Using ERE-based luciferase reporter assays, we have demonstrated that the G-1 compound for example does not activate transcription of the ERE-reporter plasmid, where estrogen itself yields a robust response (not shown). This assay, which assesses activity on an hour-day basis, reveals the ability of compounds according to the present invention to activate transcription through classical estrogen receptors (a much more sensitive assay potentially than ligand binding). Understanding multiple aspects of signaling initiated by novel compounds will provide important structure-activity relationship data that will feed back into the design of subsequent compounds.

Endogenous Receptor Function.

In addition to transfected cells, which express high levels of the transfected receptor, we also assess receptor function in endometrial and breast cancer cells. Hec50 (human endometrial cancer) and SKBr3 (breast cancer) cells are both deficient in classical ER expression (both ERα and ERβ) and have therefore frequently been termed estrogen unresponsive. Our data however, shows that both of these cell lines express GPR30 and respond to estrogen exclusively through this receptor (as demonstrated by the lack of estrogen signaling in cells transfected with GPR30 antisense constructs). To confirm the activity of novel compounds observed in transfected cells, selected experiments (e.g. PI3K activation, ERK/

EGFR phosphorylation) are repeated and extended in cells expressing endogenous GPR30.

Cellular Functions.

In addition to molecular interactions, it is necessary to characterize how the novel synthetic compounds, as well as compounds derived from biomolecular screening, modulate cellular functions. Our preliminary data suggest that G-1 may exert regulatory effects on cell growth and/or apoptosis as well as migration [Bologa, et al. *Nat Chem Biol* 2, 207-12. (2006)]. Thus, an anticipated outcome of this research may be the development of GPR30-specific compounds that can be used as chemotherapeutic agents, in addition to their use as tools to probe GPR30 biology and physiology. Examples of cellular assays are provided below.

Cell Proliferation and Apoptosis.

Both transfected cells (expressing exclusively GPR30 or ERα, ERβ) and cells expressing only endogenous receptors (SKBr3 or MCF7 cells) are used to determine the effects of novel compounds on cell viability parameters. Cell-based studies are performed using charcoal-coated dextran-treated serum to deplete all steroids from the medium. Cells are washed 4-5 times and cultured in this minimal medium for greater than 24 hours prior to use. Growth rate experiments are carried out in the presence or absence of the compound to be tested and compared to replenishment conditions where estrogen (and other steroids) have been restored to the medium. Effects are evaluated following 2-4 days incubation by crystal violet staining to determine increases in cell number. Induction of apoptosis is evaluated using AnnexinV/propidium iodide staining.

Cell Migration.

Migration assays are carried out using 6.5 mm Transwell chambers with an 8 μm pore size filter (Costar Corning Inc.). The undersurface of the filter is coated overnight at 4° C. with approximately 50 μg/ml rat-tail collagen and washed with PBS. DMEM/F12 (600 μl) supplemented with 10% FBS, 10 ng/ml of EGF and 10 μg/ml of insulin is added to the lower chamber as chemoattractant. SKBr3 or MCF7 cells (75,000 cells) in serum-free DMEM/F12 (150 μl) are treated with ethanol (control), 17β-estradiol or test compound for 15 min at 37° C. prior to loading in the upper chamber. Following incubation for 48 hours at 37° C., the remaining cells were wiped from the upper surface of the membrane with a damp cotton swab. The migrated cells on the undersurface of the membrane are fixed with 2% paraformaldehyde and stained with 1% crystal violet. Quantitation of cells is performed by counting the number of cells/field in 5 random fields per membrane and migration is calculated as: % migration=(number of cells in treated/number of cells in ethanol control)×100.

Other Activity.

Some of the compounds according to the present invention exhibit activity in some cellular assays but not others. This is similar in concept to the idea of SERMs or the increasing number of GPCR ligands that selectively activate only a subset of effectors pathways (a phenomenon termed agonist trafficking [Kenakin, *Trends Pharmacol Sci* 24, 346-54 (2003) and Vaquelin and Van Liefde, *Fundam Clin Pharmacol* 19, 45-56.(2005)]. As opposed to being a pitfall, this activity results in adding to the depth of the structure activity analyses and understanding of GPR30 function.

The present invention is illustrated by the preceding examples. It is to be understood that the particular examples, materials, amounts, and procedures are to be interpreted broadly in accordance with the scope and spirit of the invention as set forth herein.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

The invention claimed is:

1. A compound according to the chemical structure:

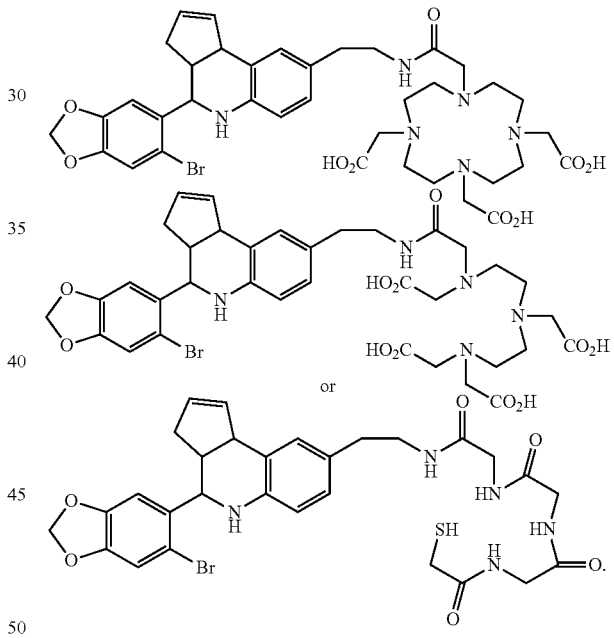

2. A compound according to any one of the following chemical structures:

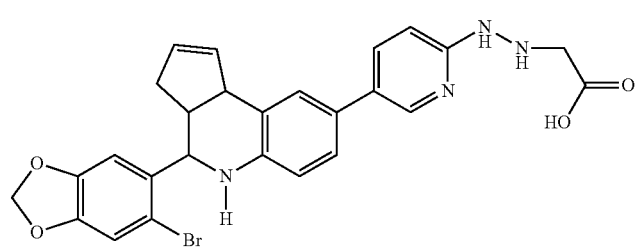

-continued
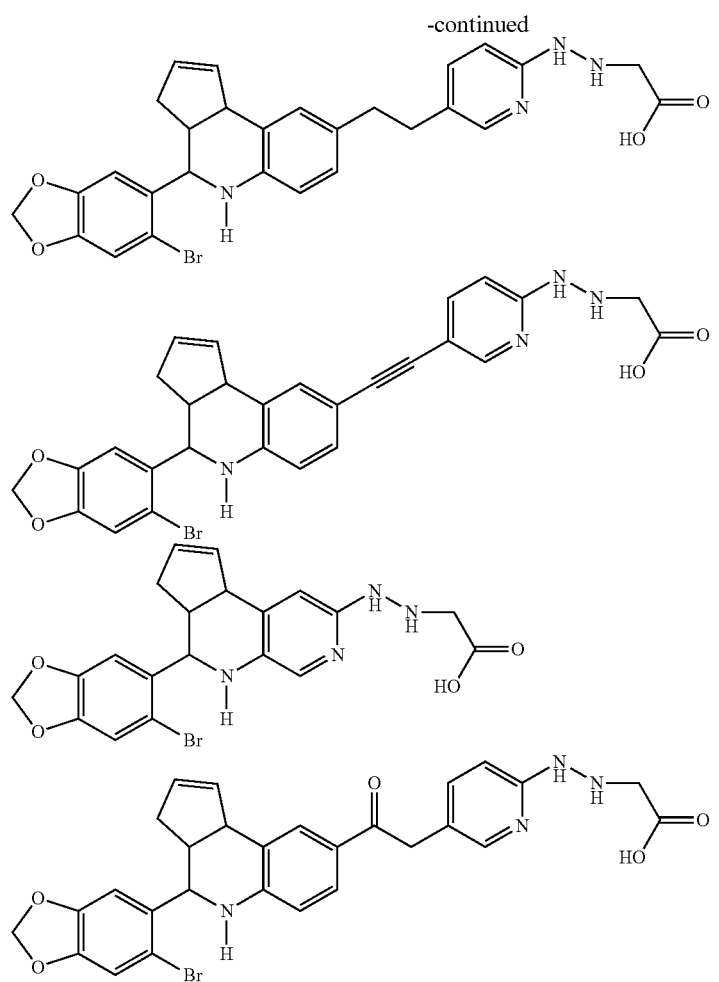
or
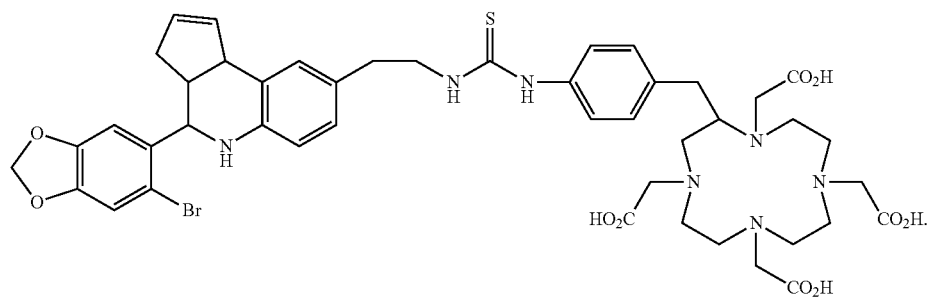
* * * * *